US009765297B2

(12) United States Patent
Przedborski et al.

(10) Patent No.: US 9,765,297 B2
(45) Date of Patent: Sep. 19, 2017

(54) STEM CELL-BASED CULTURE SYSTEM FOR DRUG DEVELOPMENT

(75) Inventors: Serge Przedborski, New York, NY (US); Hynek Wichterle, New York, NY (US); Makiko Nagai, Okayama (JP); Thomas M. Jessell, Bronx, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 1031 days.

(21) Appl. No.: 12/450,830

(22) PCT Filed: Apr. 10, 2008

(86) PCT No.: PCT/US2008/059883
§ 371 (c)(1),
(2), (4) Date: Jun. 21, 2010

(87) PCT Pub. No.: WO2008/127974
PCT Pub. Date: Oct. 23, 2008

(65) Prior Publication Data
US 2010/0267073 A1 Oct. 21, 2010

Related U.S. Application Data

(60) Provisional application No. 60/915,837, filed on May 3, 2007, provisional application No. 60/911,824, filed on Apr. 13, 2007.

(51) Int. Cl.
*C12Q 1/02* (2006.01)
*C12N 5/079* (2010.01)
*C12N 5/0793* (2010.01)

(52) U.S. Cl.
CPC ........ *C12N 5/0619* (2013.01); *C12N 2502/08* (2013.01); *C12N 2506/02* (2013.01)

(58) Field of Classification Search
None
See application file for complete search history.

(56) References Cited

U.S. PATENT DOCUMENTS

| | | | |
|---|---|---|---|
| 5,753,506 A | 5/1998 | Johe | |
| 5,817,773 A | 10/1998 | Wilson et al. | |
| 5,844,079 A | 12/1998 | Ingham et al. | |
| 5,851,832 A | 12/1998 | Weiss et al. | |
| 5,980,885 A | 11/1999 | Weiss et al. | |
| 6,040,180 A | 3/2000 | Johe | |
| 6,277,820 B1 | 8/2001 | Rosenthal et al. | |
| 6,294,346 B1 | 9/2001 | Weiss et al. | |
| 6,432,711 B1 | 8/2002 | Dinsmore et al. | |
| 6,552,016 B1 | 4/2003 | Baxter et al. | |
| 6,613,798 B1 | 9/2003 | Porter et al. | |
| 6,646,113 B1 | 11/2003 | Charroux et al. | |
| 6,683,108 B1 | 1/2004 | Baxter et al. | |
| 6,833,269 B2 | 12/2004 | Carpenter | |
| 7,101,709 B2* | 9/2006 | Weiss et al. .................. 435/377 |
| 7,115,653 B2 | 10/2006 | Baxter et al. | |
| 7,250,294 B2 | 7/2007 | Carpenter | |
| 7,294,510 B2 | 11/2007 | Okano et al. | |
| 7,390,659 B2 | 6/2008 | Jessell et al. | |
| 7,632,679 B2 | 12/2009 | Jessell et al. | |
| 7,632,680 B2 | 12/2009 | Neuman et al. | |
| 2002/0009743 A1 | 1/2002 | Carpenter | |
| 2002/0151056 A1 | 10/2002 | Sasai et al. | |
| 2003/0068819 A1 | 4/2003 | Zhang et al. | |
| 2003/0118566 A1 | 6/2003 | Neuman et al. | |
| 2004/0014210 A1* | 1/2004 | Jessell .................. C12N 5/0619 435/368 |
| 2004/0023949 A1 | 2/2004 | Baxter et al. | |
| 2004/0224302 A1 | 11/2004 | Jessel et al. | |
| 2005/0014796 A1 | 1/2005 | Baxter et al. | |
| 2005/0019801 A1 | 1/2005 | Rubin et al. | |
| 2005/0080138 A1 | 4/2005 | Guicherit et al. | |
| 2005/0203014 A1 | 9/2005 | Rubin | |
| 2005/0266555 A1 | 12/2005 | Lu et al. | |
| 2006/0275290 A1 | 12/2006 | Barbeito et al. | |
| 2006/0281179 A1 | 12/2006 | Sasai et al. | |
| 2007/0185024 A1 | 8/2007 | Jessell et al. | |
| 2007/0224650 A1 | 9/2007 | Jessell et al. | |
| 2010/0196332 A1 | 8/2010 | Wichterle et al. | |

FOREIGN PATENT DOCUMENTS

EP 1500399 A1 * 1/2005 ............. A61K 39/00

OTHER PUBLICATIONS

PCT International Preliminary Examination Report issued Jun. 13, 2005, in connection with PCT/US03/20399.
PCT International Preliminary Report on Patentability issued on Jul. 10, 2007 in connection with PCT/US05/05166.
PCT International Preliminary Report on Patentability issued on Jul. 17, 2007 in connection with PCT/US05/005877.
PCT International Preliminary Report on Patentability issued on Oct. 13, 2009 in connection with PCT/US08/59883.
PCT International Search Report issued Jun. 14, 2007 in connection with PCT/US05/05166.
PCT International Search Report issued on Oct. 7, 2004 in connection with PCT/US03/20399.
PCT International Search Report published on Jun. 26, 2007 in connection with PCT/US05/005877.
PCT International Search Report published on Jun. 30, 2008 in connection with PCT/US08/59883.
Written Opinion of International Searching Authority issued on Jun. 14, 2007 in connection with PCT/US05/05166.
Written Opinion of International Searching Authority issued on Jun. 26, 2007 in connection with PCT/US05/005877.

(Continued)

*Primary Examiner* — Laura Schuberg
(74) *Attorney, Agent, or Firm* — John P. White; Cooper and Dunham LLP

(57) ABSTRACT

The present invention relates to culture systems comprising differentiated stem cells, that may be used for identifying agents useful in treating degenerative nervous system disorders and are suitable for high-throughput screening applications. It is based, at least in part, on the discovery that co-cultures of (i) astrocytes expressing a mutated SOD1 gene and (ii) stem-cell derived motor neurons manifested cell death via a Bax-dependent mechanism, and modeled motor neuron death in amyotrophic lateral sclerosis.

4 Claims, 12 Drawing Sheets

(56) References Cited

OTHER PUBLICATIONS

Written Opinion of International Searching Authority issued on Jun. 30, 2008 in connection with PCT/US08/59883.
Supplementary European Search Report issued on Jun. 19, 2009 in connection with European Application No. 05723654.9.
Bain, G, et al. (1995) "Embryonic stem cells express neuronal properties in vitro." Dev Biol. 168:342-357.
Briscoe, J, et al. (2000) "A homeodomain protein code specifies progenitor cell identity and neuronal fate in the ventral neural tube." Cell. 101:435-445.
Briscoe, J, et al. (2001) "Specification of neuronal fates in the ventral neural tube." Curr. Opin. Neurobiol. 11:43-49.
Carpenter et al. (2001) "Enrichment of neurons and neural precursors from human embryonic stem cells", Experimental Neurology, 172(2):383-397.
Castelo-Branco et al. (2003) "Differential regulation of midbrain dopaminergic neuron development by Wnt-1, Wnt-3a, and Wnt5a", PNAS, 100(22):12747-12752.
Dann et al. (2001) "Insights into Wnt binding and signaling from the structures of two Frizzeled cysteine-rich domains" Nature, 412:86-90.
Gage, FH. (2000) "Mammalian neural stem cells." Science. 287: 1433-1438.
Harper JM, et al. (2004) "Axonal growth of embryonic stem cell-derived motoneurons in vitro and in motoneuron-injured adult rats," Proc Natl Acad Sci USA. 101:7123-7128.
Hollyday, M. (1980) "Motoneuron histogenesis and the development of limb innervations." Curr Top Dev Biol. 15(1):181-215.
Hollyday, M. (1980) "Organization of motor pools in the chick lumbar lateral motor column." J Comp Neurol. 194:143-70.
Hollyday, M., et al. (1990) "Location of motor pools innervating chick wing." J Comp Neurol. 302:575-588.
Jessell, TM. (2000) "Neuronal specification in the spinal cord: inductive signals and transcriptional codes." Nat Rev Genet. 1:20-29.
Kawasaki et al. (2000) "Induction of midbrain dopaminergic neurons from ES cells by stromal cell-derived inducing activity", Neuron, 28:31-40.
Lee, H, et al. (Aug. 2007) "Directed differentiation and transplantation of human embryonic stem cell-derived motorneurons." Stem Cells. 8:1931-9.
Lee, SK, et al. (2001) "Transcriptional networks regulating neuronal identity in the developing spinal cord." Nat Neurosci 4 Suppl. 1183-1191.
Li XJ, et al. (2005) "Specification of motorneurons from human embryonic stem cells." Nat. Biotechnol. 23(2):215-21.
Li XJ, et al. (Jan. 2008) "Directed Differentiation of Ventral Spinal Progenitors and Motor Neuron from Human Embryonic Stem Cells . . . " Stem Cells. 26(4):886-93.
Lim UM, et al. (Nov. 2006) "Derivation of Motor Neurons from three Clonal Human Embryonic Stem Cell Lines," Curr Neurovasc Res. 3(4):281-8.
Miles GB, et al. (2004) "Functional properties of motoneurons derived from mouse embryonic stem cells." J Neurosci. 24:7848-7858.
Mizuguchi, R, et al. (2001) "Combinatorial roles of olig2 and neurogenin2 in the coordinated induction of pan-neuronal . . . " Neuron. 31:757-771.
Mizuseki, K, (May 2003) "Generation of neural crest-derived peripheral neurons and floor plate cells from mouse . . . " Proc Natl Acad Sci USA. 100(100):5828-33.
Muhr, J, et al. (1999) "Convergent inductive signal specify midbrain, hindbrain, and spinal cord identity in gastrula stage chick embryos." Neuron. 23:689-702.
Munoz-Sanjuan, I, et al. (2002) "Neural induction, the default model and embryonic stem cells." Nat Rev Neurosci. 3:271-280.
Muroyama et al. (2004) "Wnt proteins promote neuronal differentiation in neural stem cell culture", Biochemical and biophysical Research Communications, 313:915-921.
Novitch, BG, et al. (2003) "A requirement for retinoic acid-mediated transcriptional activation in ventral neural patterning and motor neuron specification." Neuron. 40:81-95.
Renoncourt, Y, et al. (1998) "Neurons derived in vitro from ES cells express homeoproteins characteristic of motoneurons and interneurons." Mech Dev. 79:185-197.
Shin et al. (2007) "Stage-Dependent lig2 Expression in Motor Neurons and Oligodendrocytes Differentiated from Embryonic Stem Cells", Stem Cells and Development, 16:131-141.
Shin et al., (2005) "Human Motor Neuron Differentiation from Human Embryonic Stem Cells." Stem Cells and Development. 14:1-4.
Sounderarajan, et al. (2007) "Easy and Rapid Differentiation of Embryonic Stem Cells into Functional Motoneurons Using Sonic Hedgehog . . . " Stem Cells 25(7):1697-1707.
Tropepe, V, et al. (2001) "Direct neural fate specification from embryonic stem cells: a primitive mammalian neural stem cell stage" Neuron 30:65-78.
Uchida, N, et al. (2000) "Direct isolation of human central nervous system stem cells." Proc Natl Acad Sci USA. 97:14720-14725.
Wichterle, H, et al. (2002) "Directed differentiation of embryonic stem cells into motor neurons." Cell. 110:385-397.
Wichterle, H, et al. (2008) "Differentiation of mouse embryonic stem cells to spinal motor neurons." In Current Protocols in Stem Cell Biol. Chap. 1:Unit 1H.1.1-1H.1.9.
Wichterle, H, et al. (2009) "Xenotransplantation of Embryonic Stem Cell-Derived Motor Neurons . . . " In Stem Cells in Regenerative Medicine 171-183.
Zhou, Q, et al. (2002) "The bHLH transcription factors OLIG2 and LIG1 couple neuronal and glial subtype specification." Cell. 109: 61-73.
International Search Report issued by the International Searching Authority (ISA/US) on Jun. 30, 2008 in connection with International Application No. PCT/US2008/059883.
Written Opinion of the International Searching Authority issued by the International Searching Authority (ISA/US) on Jun. 30, 2008 in connection with International Application No. PCT/US2008/059883.

\* cited by examiner

Figure 1A-H
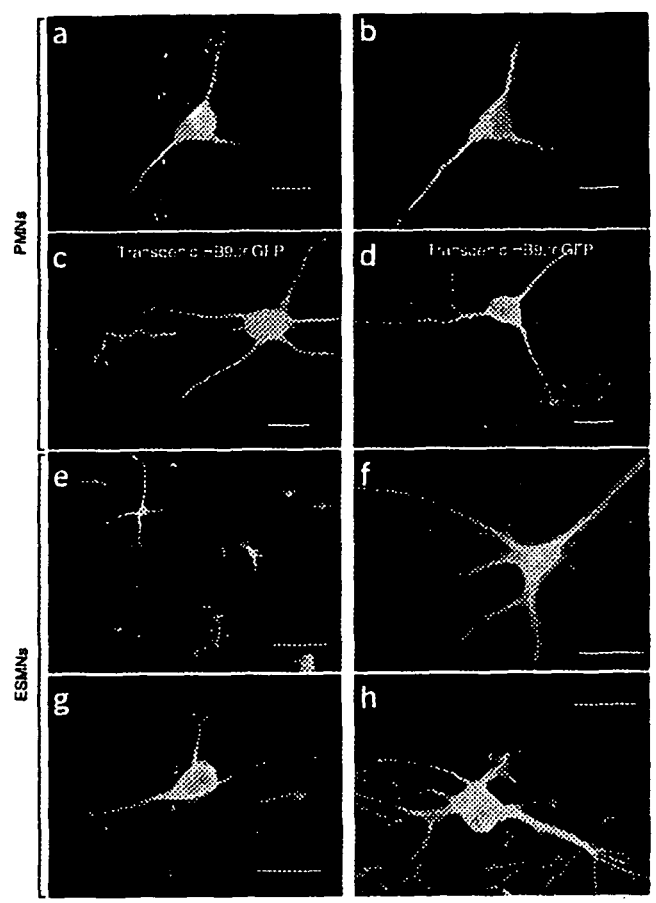

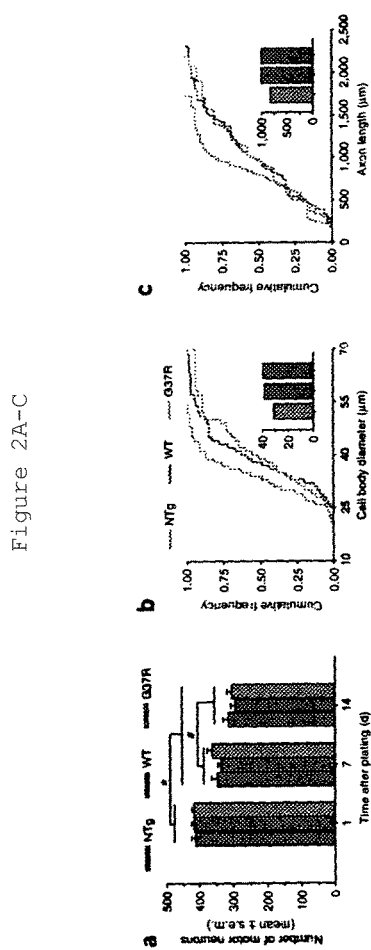
Figure 2A-C

Figure 3A-G
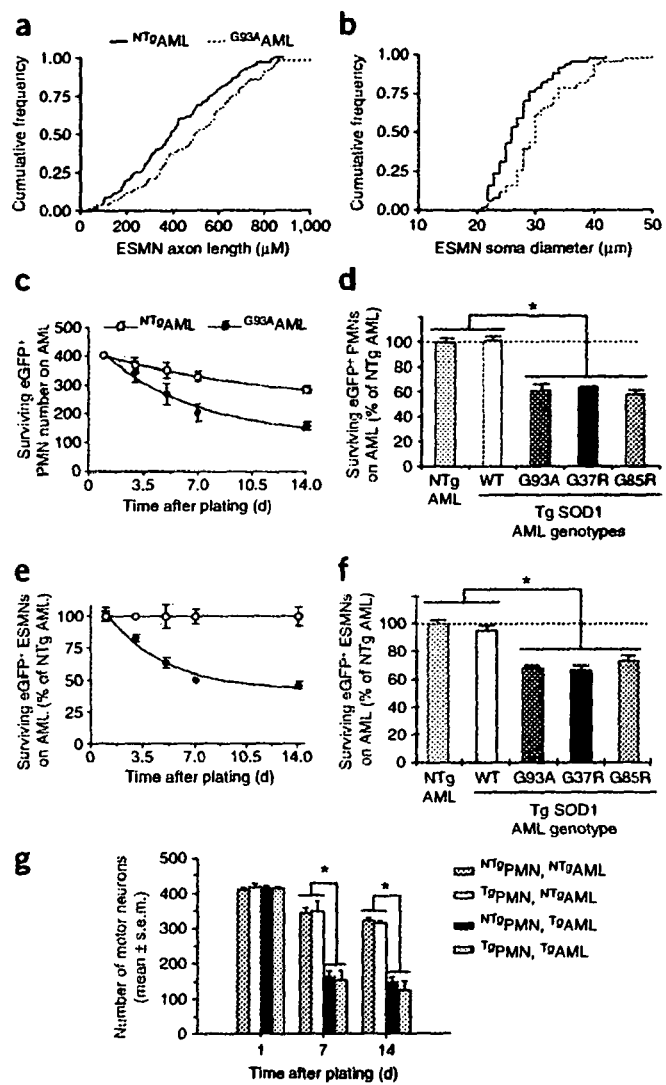

Figure 4A-C
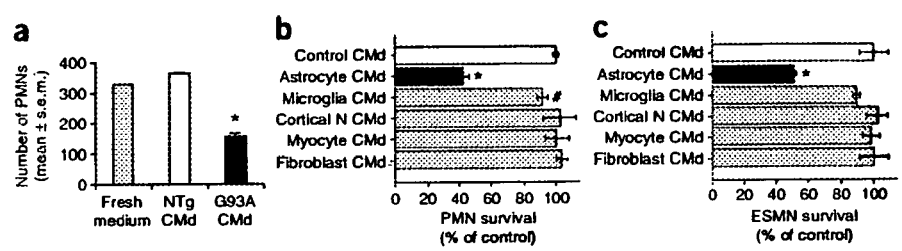

Figure 5A-H
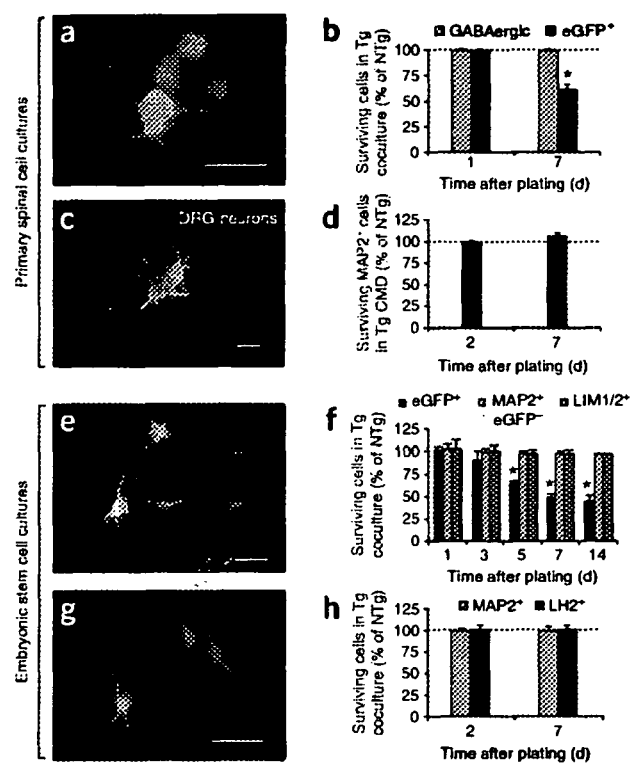

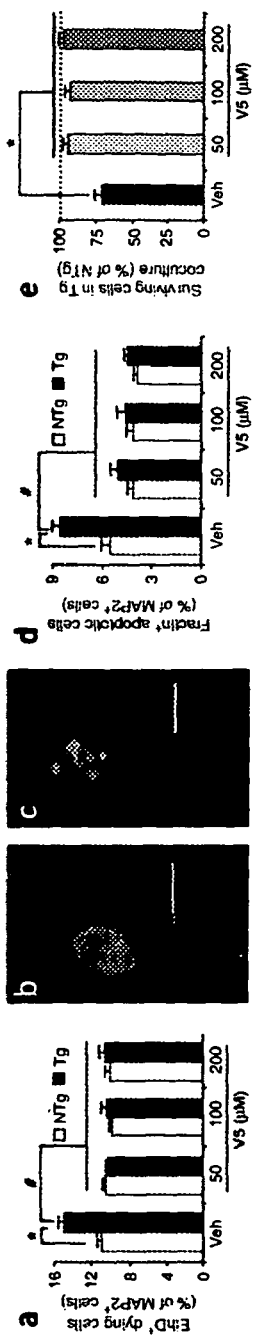
Figure 6A-E

Figure 7A-E
a
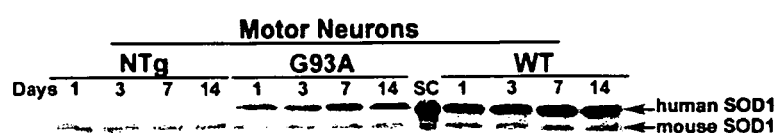
b
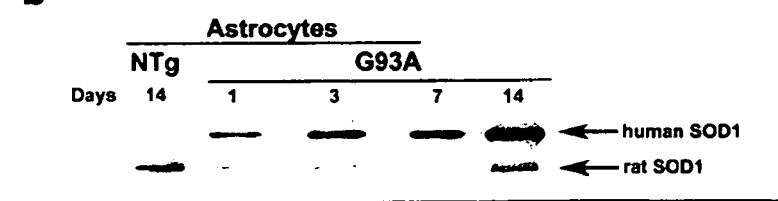
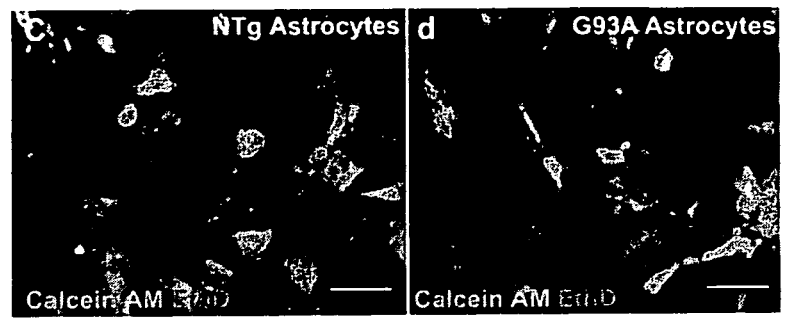
e
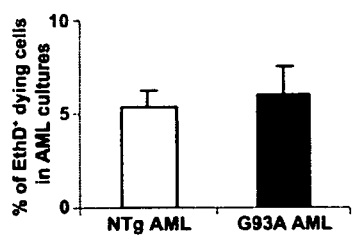

Figure 8A-B
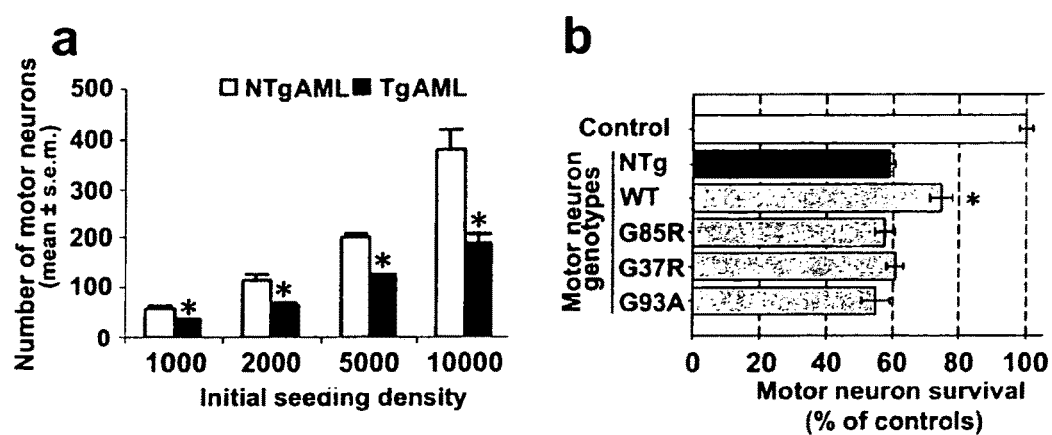

Figure 9A-B
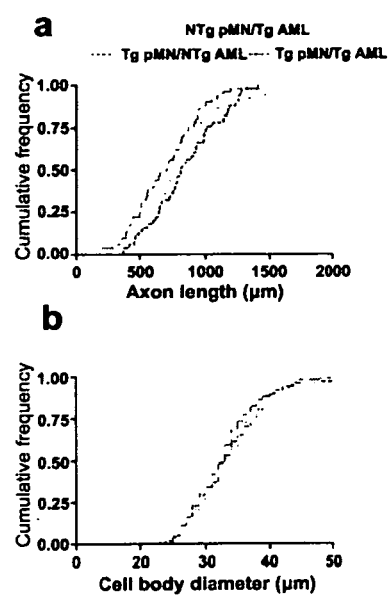

Figure 10A-B
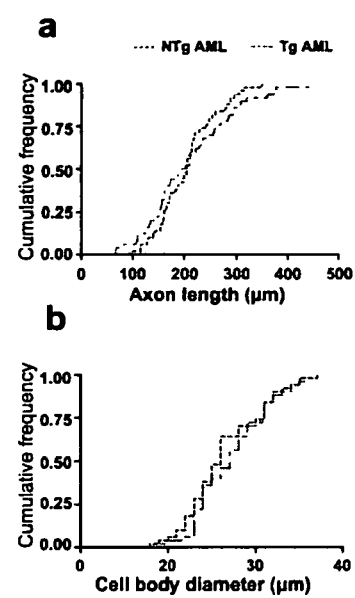

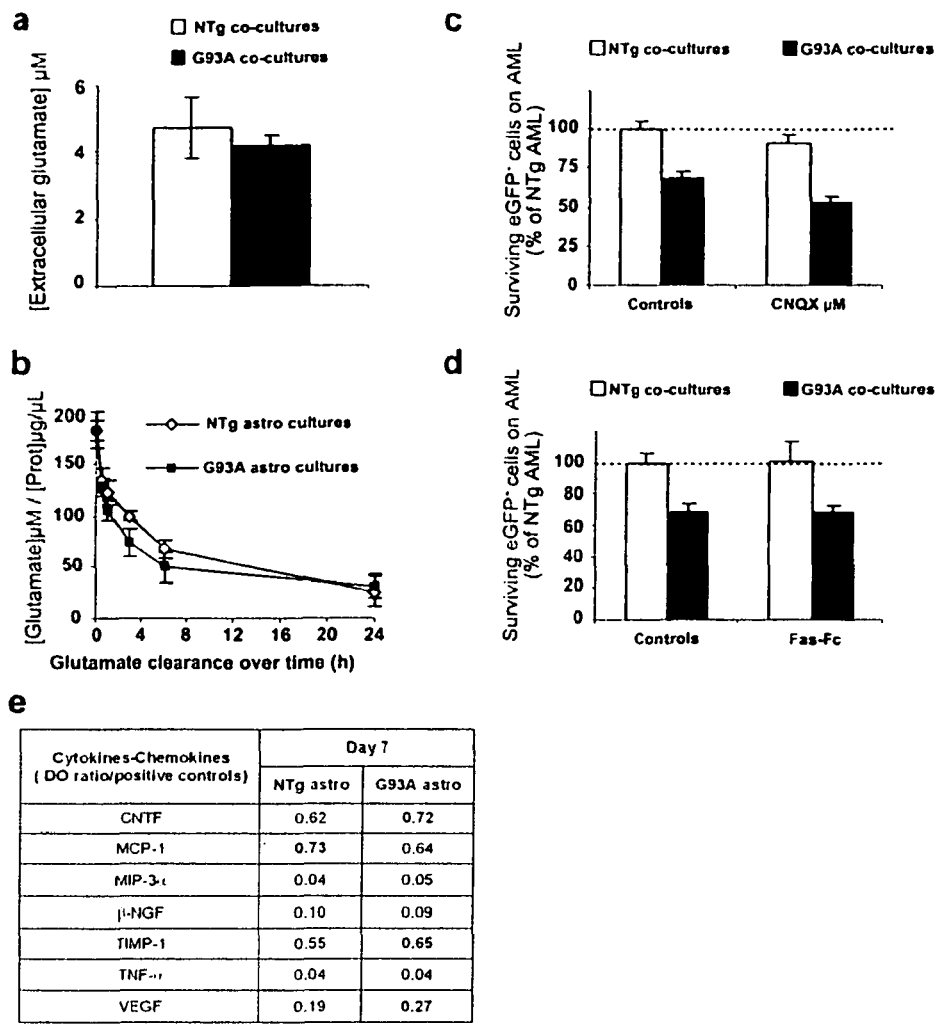
Figure 11A-E

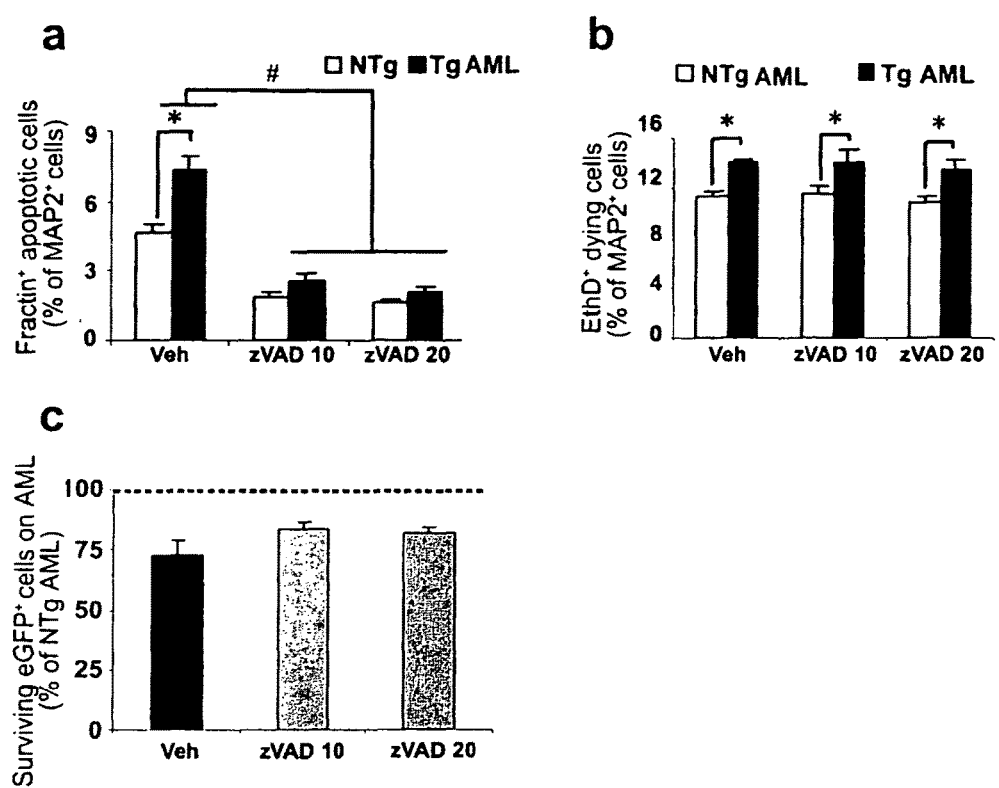
Figure 12A-C

STEM CELL-BASED CULTURE SYSTEM FOR DRUG DEVELOPMENT

CROSS-REFERENCE TO RELATED APPLICATIONS

This application is a §371 national stage application of PCT International Application No. PCT/US2008/059883, filed Apr. 10, 2008, and claims the benefit of U.S. Provisional Applications Nos. 60/915,837, filed May 3, 2007 and 60/911,824, filed Apr. 13, 2007, the contents of all of which are hereby incorporated by reference into this application.

GRANT SUPPORT

This invention was made with government support under Grant Nos. NS42269, NS38370, NS11766, AG 21617, ES013177 and DK58056 awarded by the United States National Institutes of Health and Grant No. DAMD 17-03-1 awarded by the United States Department of Defense. The government has certain rights in the invention.

1. INTRODUCTION

The present invention relates to culture systems, comprising differentiated stem cells, that may be used for identifying agents useful in treating degenerative nervous system disorders and are suitable for high-throughput screening applications.

2. BACKGROUND OF THE INVENTION

2.1 Amyotrophic Lateral Sclerosis

Amyotrophic lateral sclerosis (ALS) is a relentless fatal paralytic disorder confined to the voluntary motor system [37]. The onset of disease is usually in the fourth or fifth decade of life. Common clinical features of ALS include muscle weakness, fasciculations, brisk (or depressed) reflexes, and extensor plantar responses. Although motor deficit usually predominates in the limbs, bulbar enervation can be severely involved, sometimes early in the course of the disease, leading to atrophy of the tongue, dysphagia, and dysarthria. Other cranial nerves (e.g., occulomotor nerves) are usually spared, unless the patient survives beyond respiratory failure [38]; this latter is due to respiratory muscle paralysis that occurs frequently in advanced cases. The disease progresses rapidly, with a mean survival of 3 years. Pathologically, ALS is characterized mainly by a loss of upper motor neurons, lower motor neurons, or both [39]. To date, only a few approved treatments, such as mechanical ventilation and riluzole, do prolong survival in ALS patients to some extent. However, the development of more effective neuroprotective therapies is impeded by our limited knowledge of the actual mechanisms by which motor neurons die in ALS, and of how the disease propagates and progresses.

ALS usually arises as a sporadic condition in the absence of any apparent genetic linkage, but occasionally (in about 10 percent of cases) the disease is inherited [40]. The majority of familial forms of ALS are transmitted as autosomal dominant traits and are clinically and pathologically almost indistinguishable from sporadic ALS; however, familial ALS tends to have an earlier age of onset, a more rapid course, and a survival after diagnosis of only 1.5 years. Approximately 20 percent of familial ALS cases are linked to mutations in the gene encoding for the cytosolic enzyme SOD1 [40]. To date, more than 120 mutations in SOD1 have been identified in familial ALS families. Many of these mutations lead to the substitution of an amino acid, several of which, such as the glycine-to-alanine substitution at position 93 (G93A) and the glycine-to-arginine substitution at position 37 (G37R), are similar to wild-type SOD1 with respect to their stability, metal coordination properties and homospecific catalytic activity, whereas several others, such as the glycine-to-arginine substitution at position 85 (G85R), exhibit poor stability and low catalytic activity [41].

For more than a decade, the lion's share of attention in ALS research has been paid to mutant SOD1. The rationale for studying so avidly this rare form of ALS rests on the expectation that the phenotypic similarity between the genetic and sporadic forms of the disease indicates that they share important pathogenic mechanisms and, consequently, that information generated by studying mutant SOD1 will help focus research on key cellular and molecular mechanisms.

SOD1 is an abundant, ubiquitously expressed cytosolic enzyme whose known activity is to dismutate superoxide to hydrogen peroxide. Although SOD is thought to be essential for living organisms [42], mutant mice deficient in this enzyme thrive normally and do not develop a ALS phenotype [43]. Conversely, Tg (Tg) rodents expressing either catalytically active SOD1 mutants [3; 4] or catalytically inactive SOD1 mutants [5; 44] recapitulate the clinical and the neuropathological hallmarks of ALS. Transgenic (Tg) mice expressing high levels of wild-type human SOD1 are healthy [3]. Taken together, these results argue for mutant SOD1 causing motor neuron degeneration, not via a loss-of-, but rather via a gain-of-function effect. However, despite intense research efforts, the nature of the adverse property manifested by mutant SOD1 remains elusive. To date, it has been proposed that mutant SOD1 cytotoxicity involves different mechanisms including oxidative stress [45, 46], protein aggregation [14], aberrant protein-protein interactions [48], decreased binding affinity for zinc [49], mitochondrial dysfunction [50], and apoptosis [9, 51], none of which are mutually exclusive, Aside from the mechanism of toxicity, the mutant SOD1 cellular site of action is also a source of discussion. For instance, several recent studies support the notion that mutant SOD1 in both motor neurons and non-neuronal cells contribute to the disease process in vivo [52, 53, 8]. Indeed, it has been shown that both the selective lowering of mutant SOD1 in either motor neurons or in glial cells such as microglia by a Cre-Lox system prolongs survival in Tg SOD1G37R mice compared to their germline littermates [8]. Similarly, PU.1-deficient mice carrying the SOD1G93A mutation, and in which the lack of microglia is corrected by transplantation of wild-type bone marrow cells, have a longer lifespan than those transplanted with SOD1G93A bone marrow cells [53]. Furthermore, studies in chimeric mice [20] composed of cells expressing either wild-type or mutant SOD1 observed that: (i) a greater fraction of mutant motor neurons survived when surrounded by wild-type cells; and, (ii) wild-type motor neurons surrounded by non-neuronal cells expressing mutant SOD1 did acquire ubiquitin-positive protein aggregates, a sign of neuronal damage in this ALS model [9]. In a model system of a different form of neurodegeneration, an effect of supporting cells on nearby neurons has also been observed: it has been shown that expression of mutant ataxin-7 in astrocytes causes degeneration of wild-type Purkinje cells in a mouse model of spinocerebellar atrophy [10].

As indicated above, deletion of mutant SOD1 in microglia [22] or absence of microglia expressing mutant SOD1 [53] prolonged survival in Tg mutant SOD1 mice. However, this did not delay the age at onset of symptoms. Furthermore, mutant SOD1 microglia did not induce the death of wild-type motor neurons in vivo [53].

2.2 Spinal Muscular Atrophy

Aside from ALS, there are several other types of prominent motor neuron disease [37]. Among these, spinal muscular atrophy ("SMA") is the most common fatal neurodegenerative disease of infancy, with an incidence of 1 in 6,000 [54]. This autosomal recessive disease maps to the proximal region of the long arm of chromosome 5, which contains two, almost identical, genes termed "survival of motor neuron" (SMN) genes [55]. In 95 percent of the SMA patients, there is a large-scale deletion of the telomeric copy of SMN, designated SMN1, whereas, in the 5 percent remaining, there is a point mutation in or a short deletion of SMN1 [26]. These observations led to the conclusion that SMN1 is a determining gene in SMA. Conversely, it was found that SMA patients always carry at least one copy of SMN in the form of a centromeric copy, designated SMN2 [54]. This gene, however, is only partially functional, and thus SMN2 is unable to fully compensate for the SMN1 defect [54]. Notably, due to the unstable nature of the genome that contains the SMN genes, SMA patients can carry more than one copy of SMN2 [54] and the greater the number of SMN2 copies, the milder the disease phenotype [56]. For instance, 80 percent of patients with type-I SMA (i.e. severe weakness, profound hypotonia, and a mortality usually due to respiratory failure within the 2 first years of life) carry one or two SMN2 copies; 82 percent of patients with type-II SMA (i.e. disability of later onset, less severe weakness, and survival into adolescence and beyond) carry three SMN2 copies; and, 96 percent of patients with type-III SMA (i.e. onset usually in adolescence or youth adulthood, mild weakness allowing an achievement of ambulation and a normal survival expectancy) carry three or four SMN2 copies [56]. Therefore, SMN2 is not a SMA-causing gene, but it is an important disease modifier, a concept that has been confirmed in engineered mice [57].

While significant strides have been made over the past decade in unraveling the neurobiology of SMA, the function of the SMN protein still remains incompletely elucidated [54]. SMN is ubiquitously expressed and, if knocked out, any cell type would die [58]. This provides compelling evidence that SMN plays a vital role and, by now, it is well established that, through its binding capacity to ribonucleoproteins, SMN is essential to the assembly of the proper Sm core protein to small nuclear RNAs [59]. In addition to its critical role in the biogenesis of the small nuclear ribonucleoproteins, SMN also participates in the maturation of pre-mRNA [60]. However, SMN binds to several other partners [61-64] whose functions are distinct from that of small nuclear ribonucleoprotein biogenesis and pre-mRNA splicing, hence supporting the notion that SMN must be endowed with other important, and for the moment unknown, cellular roles.

Another unsettled question about SMN is: why does a ubiquitously expressed protein cause a motor neuron disease? It is already known that SMN is highly expressed in spinal motor neurons [54] and that lowering SMN selectively in neurons provokes their demise [36]. However, since a low level of SMN is noxious to all cells, one cannot exclude that reduced SMN levels contribute to the disease phenotype by also affecting non-neuronal cells such as glia.

3. SUMMARY OF THE INVENTION

The present invention relates to culture systems, comprising differentiated stem cells, that may be used for identifying agents useful in treating degenerative nervous system disorders and that are suitable for high-throughput screening applications. It is based, at least in part, on the discovery that co-cultures of (i) astrocytes expressing a mutated SOD1 gene and (ii) stem-cell derived motor neurons manifested motor neuron cell death via a Bax-dependent mechanism, and modeled motor neuron death in amyotrophic lateral sclerosis (ALS). The use of a differentiated stem cell component advantageously allows the preparation of multiple cultures which may be processed in parallel, wherein each culture is essentially the same and therefore affords, in addition to scalable production, results which are scientifically reliable (because there is a valid basis for comparing one culture to another) and reproducible. Accordingly, the present invention provides for assay systems that may be used to identify agents to treat neurodegenerative conditions, particularly ALS.

4. BRIEF DESCRIPTION OF THE FIGURES

FIG. 1a-e. (a,b) Immunostaining of primary neuronal cultures showing MAP2$^+$/HB9$^+$ (a) and SMI32$^+$/HB9$^+$ large multipolar pMN (b) derived from non-transgenic (NTg) mouse embryos. Identical pMN were derived from transgenic (Tg) human SOD1$^{WT}$ and SOD1$^{G37R}$ mouse embryos (not shown). All were plated on NTg astrocyte monolayers. (c,d) Double immunostaining of primary neuronal cultures showing a MAP2$^+$/eGFP$^+$ (c) and a ChAT$^+$/eGFP$^+$ (d) pMN derived from a transgenic Hlxb9-GFP1Tmj embryo. (e-h) ESMN expressing eGFP under the HB9 promoter were cultured for 7 d on spinal cord astrocyte monolayers. Confirming their motor neuron phenotype, eGFP$^+$/HB9$^+$ ESMN are immunopositive for MAP2 (e, f), ChAT (g) and Islet 1/2 (h). Scale bar=50 μm (a,b,c,d,f,g,h) and 100 μm (e).

FIG. 2a-c. Mutant SOD1 expressed in primary spinal-cord motor neurons provokes a mild cell-autonomous phenotype. (a) Quantification of $^{NTg}$, $^{WT}$ and $^{G37R}$pMN at 1, 7 and 14 d post-plating revealing progressive decreases ($p<0.01$) in pMN numbers, but no difference among the various genotypes ($p>0.05$). Values represent means±s.e.m. from at least 3 independent experiments performed at least in triplicate. Analyses were done by two-way ANOVA followed by a Newman-Keuls post Hoc test. (b,c) At 14 d post-plating, $^{G37R}$pMN showed (Kolmogorov-Smirnov test; $p<0.001$) smaller cell body diameters (b), and shorter axon lengths (c) compared to $^{WT}$ and $^{NTg}$pMN. Insets represent the respective medians. For these analyses, data from 50-100 motor neurons per genotype were used.

FIG. 3a-g. Marked toxicity of mutant SOD1-expressing astrocytes on primary motor neurons. (a,b) ESMN exhibit shorter axonal lengths and smaller cell body diameters when plated on mutant SOD1$^{G93A}$-expressing astrocyte monolayers (AML) compared to their counterparts plated on $^{NTg}$AML (Kolmogorov-Smirnov test; $p<0.005$). At 14 d in culture, similar alterations are observed in pMN plated on mutant $^{G93A}$AML (not shown). (c) The decay of $^{eGFP+}$pMN plated on $^{G93A}$AML is greater ($F_{[3, 37]}=6.3$, $p=0.0015$) than that of $^{eGFP+}$pMN plated on $^{NTg}$AML. (d) At 7 d post-plating, there is consistently fewer $^{eGFP+}$pMN ($p<0.01$) in $^{G93A}$AML co-cultures than in $^{NTg}$AML co-cultures. Like $^{G93A}$AML co-cultures, $^{G37R}$ and $^{G85R}$AML co-cultures have fewer $^{eGFP+}$pMN ($p<0.01$) 7 d post-plating. However, $^{WT}$ and $^{NTg}$AML co-cultures have similar ($p>0.05$) numbers of $^{NTg}$pMN. (g) To test the difference between combinations, co-cultures were made of $^{NTg}$ or $^{G37R}$pMN plated on $^{NTg}$ or $^{G93A}$AML. There are comparable numbers ($p>0.05$) of surviving $^{NTg}$ or $^{G37R}$pMN plated on $^{NTg}$AML at all time points. There are fewer (p<0.01) surviving $^{NTg}$ or $^{G37R}$pMN plated on $^{G93A}$AML than plated on $^{NTg}$AML. The loss of $^{G37R}$pMN is comparable (p>0.05) to that of $^{NTg}$pMN when plated on $^{G93A}$AML. (e,f) ESMN plated on either $^{NTg}$ or $^{G93A}$AML behave as pMN. Values represent means±s.e.m. from at least 3 independent experiments performed at least in triplicate. Analyses were done by two-way ANOVA followed by a Newman-Keuls post Hoc test.

FIG. 4a-c. Media conditioned specifically with astrocytes expressing mutant SOD1 kill primary spinal cord and embryonic stem cell-derived motor neurons. (a) $^{eGFP+}$pMN were plated on poly-D-lysine/laminin-coated cover slips and cultured for seven d. This shows that the numbers of surviving $^{eGFP+}$pMN cultured with fresh medium or with conditioned medium (CMd) from $^{NTg}$AML are higher than those cultured with $^{G93A}$AML CMd (p<0.05). (b,c) In contrast to the $^{G93A}$AML CMd, media conditioned with $^{G93A}$cerebral cortex neurons, $^{G93A}$skeletal myotubes, or $^{G93A}$skin fibroblasts have no effect (p>0.05) on either pMN or ESMN survival compared to control (ESMN cultured with medium conditioned with NTg cells). Media conditioned with spinal $^{G93A}$microglia plated at a density twice that of astrocytes exhibit only mild toxic effects on pMN (p<0.05) or ESMN (p>0.05) survival. Values represent means±s.e.m. from at least 3 independent experiments performed at least in triplicate. Analyses were done by two-way ANOVA followed by a Newman-Keuls post Hoc test.

FIG. 5a-h. Neither mutant SOD1 astrocyte monolayers nor conditioned media impair survival of neurons other than motor neurons. (a) $^{eGFP+}$pMN on AML were immunostained for eGFP and GABA at 7 d. (b) The percentage of surviving $^{eGFP+}$pMN on $^{G93A}$AML for 7 d are fewer (p<0.004) than those for 1 d while that of surviving GABA$^+$ neurons on $^{G93A}$AML are identical at 1 and 7 d (p>0.5). (c,d) The percentage of surviving DRG neurons immunostained for MAP2 cultured for 2 and 7 d with $^{G93A}$AML CMd are also identical (p>0.05). (e) Within the same culture, among the embryonic stem cell-derived MAP2$^+$ neurons, some are eGFP$^+$/HB9$^+$ (ESMN) and others are eGFP$^-$/HB9$^-$; among the latter, some express the Lim1/2 anterior interneuron marker. (f) ESMN, MAP2$^+$/eGFP$^-$/HB9$^-$ (MAP2$^+$/GFP$^-$), and MAP2$^+$/eGFP$^-$/HB9$^-$/Lim1/2$^+$ (Lim1/2$^+$) neurons were plated on $^{NTg}$ or $^{G93A}$AML. After 5 d, the percentages of surviving ESMN on $^{G93A}$AML are lower (*p<0.01) than those on $^{NTg}$AML. In contrast, neither the percentages of MAP2$^+$/GFP$^-$ (F$_{[3,24]}$=0.4, p=0.8) nor of Lim1/2$^+$ neurons (F$_{[3,16]}$=0.1, p=0.9) differ between both AML co-cultures. (g) Embryonic stem cell-derived neurons differentiated in posterior interneurons express the LH2 marker. (h) The percentages of surviving LH2$^+$ or MAP2$^+$ neurons are not decreased at 2 or 7 d (p>0.05). Values represent means±s.e.m. from at least 3 independent experiments performed at least in triplicate. We analyzed by two-way ANOVA followed by a Newman-Keuls post Hoc test. Scale bar=100 μm (a), 20 μm (c) and 50 μm (e.g.).

FIG. 6a-e. ESMN die in response to mutant AML via a Bax-dependent mechanism. (a-e) Death of ESMN was assessed by immunostaining for fractin and by ethidium bromide (EthD) uptake. (a,b) All ESMN immunopositive for fractin showed DNA condensations, as evidenced by Hoechst 33342 (a) and all ESMN with Hoechst 33342-labeled chromatin clumps show DNA fragmentation, as evidenced by TUNEL (b). At 7 d post-plating, the Bax inhibitor pentapeptide VPMLK (V5) decreases (p<0.01) the percentages of embryonic stem cell-derived MAP2$^+$/fractin$^+$ neurons (c) and ESMN labeled with EthD (d) and increases (p<0.01) the percentages of surviving ESMN (e). Values are expressed as percent of NTg values and represent means±s.e.m. from at least 3 independent experiments performed at least in triplicate. Analyses were done by two-way ANOVA followed by a Newman-Keuls post Hoc test *Higher (p<0.01) than NTg AML co-cultures; †lower (p<0.001) than vehicle (Veh; DMSO). Scale bar=20 μm (a,b).

FIG. 7a-e. Human SOD1 transgene expression is stable in both primary neuronal and astrocyte cultures over time and is harmless to astrocytes. (a-b) Immunoblots showing a stable and comparable expression of Human SOD1 (hSOD1) over 14 d in spinal neuronal (a) and astrocyte cultures (b) derived from Tg SOD1$^{G85R}$ or SOD1$^{WT}$ mouse embryos. In neuronal and astrocyte NTg cultures only endogenous mouse SOD1 (mSOD1) was detected. (c, d) Double staining of 14-d old confluent NTg and SOD1$^{G93A}$ astrocyte monolayers (AML) with the living cell probe calcein-AM and the cell death marker ethidium homodimer (EThD). (e) The number of EThD-labeled cells did not differ between NTg and Tg SOD1$^{G93A}$ astrocyte cultures (P=0.725). Values are means±sem for 3 experiments per group and the above statistics refer to Student t-test.

FIG. 8a-b. Mutant SOD1 astrocytes kill the same extent NTg and mutant SOD1 motor neurons. (a) At 7 d post-plating, there was consistently fewer SM132$^{+NTG}$pMN (P<0.01) in $^{G93A}$AML co-cultures than in $^{NTg}$AML co-cultures, and the magnitude of the genotypic difference was the same regardless of the initial motor neuron seeding densities. (b) At 7 d post-plating, the loss of $^{G93A}$, $^{G37R}$, $^{G85R}$pMN and $^{NTg}$pMN plated on $^{G93A}$AML was similar (P>0.05), but it was greater (*P<0.01) than the loss of $^{NTg}$pMN plated on $^{NTg}$AML. The loss of $^{WT}$pMN plated on $^{G93A}$AML was smaller than that of $^{G93A}$, $^{G37R}$, and $^{G85R}$pMN and $^{NTg}$pMN plated on $^{G93A}$AML and greater than that of $^{NTg}$pMN plated on $^{NTg}$AML control co-cultures (**P<0.01).

FIG. 9a-b. Mutant SOD1 expression by astrocytes, motor neurons or both alters to the same extent motor neuron morphometry. (a, b) At 7 d in culture, shorter axonal lengths and smaller cell body diameters are similarly observed in $^{G37R}$pMN plated on $^{G93A}$AML compared to $^{G37R}$pMN plated on $^{NTg}$AML (Kolmogorov-Smirnov test. P=0.358) or compared to $^{NTg}$pMN plated on $^{G93A}$AML (Kolmogorov-Smirnov test. P=0.095).

FIG. 10a-b. GABAergic interneuron morphometry is not affected by mutant SOD1-expressing astrocytes. (a, b) At 7 d in culture, GABAergic neurons plated $^{G93A}$AML or $^{NTg}$AML exhibit similar axon lengths and cell body diameters (Kolmogorov-Smirnov test. P=0.678 and p=0.241, respectively).

FIG. 11a-e. Glutamate, Fas ligand and several major cytokines and chemokines are not involved in the toxicity of mutant SOD1 astrocytes to motor neurons. (a) Extraceulluar glutamate concentrations measurement by HPLC at 7 d post-plating in co-cultures made of $^{NTg}$pMN plated on $^{NTg}$AML or $^{G93A}$AML did not differ (Student t-test; P=1.0). (b) 14 d-old-confluent $^{NTg}$AML or $^{G93A}$AML were incubated with 200 μM of glutamate. Then, the extracellular concentration of glutamate was monitored by HPLC at 0, 0.5, 1, 3, 6 and 24 hr. No interaction was found between the timing of glutamate decrease in the medium and the genotypes of the two astrocyte layers (F$_{[2,24]}$=0.430; P=0.826; ANOVA). (c) Application of 100 μM of CNQX, a potent AMPA/kainite receptor antagonist, did not influence mutant SOD1 astrocyte-mediated motor neuron death. (d) Incubation of the co-cultures with 1 μg/mL of Fas-Fc, the inhibitor of soluble Fas ligand, did not improve motor neuron survival on mutant astrocyte layer. (e) The relative contents of 19 cytokines/chemokines were screened by array in CMd from G93A and NTg astrocytes. Only, the 7 molecules with detectable quantities were reported in the table. The genotypic differences were highlighted in bold. The other 12 screened molecules with undetectable levels were CINC-2/3, Fractalkine, GM-CSF, IL-1α1β/4/6/10, IFN-γ, LIX, and Leptin.

FIG. 12a-c. Mutant SOD1-expressing astrocytes kill motor neurons through a programmed cell death which can be caspase-independent. (a-c) At 7 d post-plating, the caspase inhibitor zVAD.fmk decreased (P<0.01) the percentage of embryonic stem cell-drived MAP2$^+$/fractin$^+$ neurons (a) but had no effect on the percentage of embryonic stem cell-derived MAP2$^+$ neurons labeled with EthD (b) or of surviving ESMN (c). *Higher (p<0.01) than $^{NTg}$AML co-cultures; lower (p<0.001) than vehicle (veh; DMSO). Values are means±sem for 4-6 experiments per group and all the above statistics refer to ANOVA followed by Newman-Keuls post-hoc testing.

5. DETAILED DESCRIPTION OF THE INVENTION

The present invention relates to culture systems that comprise differentiated stem cells and methods for using such systems for identifying agents useful in treating degenerative nervous system disorders.

For clarity of description, and not by way of limitation, the detailed description is divided into the following subsections:
(i) neurodegenerative conditions for modeling by culture systems of the invention;
(ii) culture systems; and
(iii) assay methods.

5.1 Neurodegenerative Conditions for Modeling by Culture Systems of the Invention The present invention may be applied toward identifying agents useful in nervous system disorders characterized by neurodegeneration, including, but not limited to, amyotrophic lateral sclerosis (ALS), spinal muscular atrophy (SMA), Alzheimer's disease (AD), Parkinson's disease (PD), Huntington's chorea, and neurodegeneration secondary to traumatic or ischemic injury.

5.2 Culture Systems

The culture systems of the invention comprise at least two elements: first, a neuron of the type afflicted in the neurodegenerative condition of interest; and second, a component which promotes the degeneration of said neurons. The latter component may be supplied either by a cell of a type other than the neuron of interest, or a conditioned medium (or fraction thereof or compound purified therefrom) generated by a cell or cells of a type other than the neuron of interest. At least one of these two elements is derived from a stem cell, wherein the stem cell is subjected to one or more agent which causes it to differentiate toward the cell type of interest (although it need not be identical in phenotype to the naturally occurring cell type of interest—e.g., it may not be completely differentiated).

The culture systems of the invention may comprise cells and/or components originating from one species or multiple species, where such species may be, for example and not by way of limitation, rodent species including mouse and rat, or other mammalian species, including primate species such as human, monkey and chimpanzee species.

The neuron of interest in a culture system of the invention may comprise a marker which may be used to evaluate whether it is degenerating, dying, or has died. For example, but not by way of limitation, a viable cell may express a fluorescent marker, such as a Green Fluorescent Protein, Yellow Fluorescent Protein, etc., as set forth in the working example, below. In such a system, loss of fluorescence would correlate with loss of viability. Other markers may be used, for example, but not limited to, differentiated neuronal markers such as, but not limited to, microtubule-associated protein 2 (MAP2), the motor neuron-specific transcription factor HB9, the unphosphorylated neurofilament heavy chain (SM132), the cholinergic transmitter synthetic enzyme choline acetyltransferase (ChAT), the LIM homeodomain proteins Isl-1 and Isl-2, or markers of apoptosis (such as, for example, cleaved cytokeratin-18 (c-CK18), cleaved caspase-3 (c-cas-3), cleaved lamin A (c-lam-A), phosphorylated histone H2AX (H2AX), cleaved poly(ADP ribose) polymerase (c-PARP) (Holubec et al., 2005, J. Histochem. Cytochem. 53 (2): 229-235), cytosolic labile zinc, and poly-ADP ribose polymerase. Other suitable markers may reflect functionality rather than viability.

In particular, non-limiting embodiments, the present invention provides for a culture system which may be used to identify an agent useful in the treatment of a disorder characterized by motor neuron degeneration, such as, but not limited to, ALS or SMA. In this subset of embodiments, motor neurons to be used in the system may be either derived from stem cells subjected to conditions that promote motor neuron degeneration or, less preferably, may be primary motor neurons harvested in differentiated form. The motor neurons, or stem cells from which they are prepared, may derive from individuals afflicted with a neurodegenerative condition (either arising naturally or induced (as in an animal model)), but it has been unexpectedly found (see below) that motor neurons arising from normal (wild-type) individuals (or stem cells from normal individuals) may be used in the systems of the invention and, in the absence of an intervening agent, manifest degeneration and cell death. Such systems of the invention may further comprise a component which is either a degeneration-promoting astrocyte or a conditioned medium or fraction or factor derived therefrom. For example, but not by way of limitation, a degeneration-promoting astrocyte may (i) carry one of the various mutations of SOD1 associated with ALS; (ii) carry one or more mutations in the SMN gene; or (iii) may be derived from an individual having ALS or SMA. Such astrocytes may be prepared directly from a human or non-human animal, may be engineered to contain one or mutant gene associated with degeneration-promoting activity, or may be prepared by causing differentiation of stem cells. According to this subset of embodiments, in a preferred non-limiting example, the invention provides for a co-culture whereby a monolayer of degeneration-promoting astrocytes is prepared, to which motor neuron medium (and/or differentiation-promoting medium) and motor neurons (e.g., prepared from stem cells, or primary motor neurons prepared from an organism, preferably wild-type) are added. Preferably multiple parallel cultures are prepared for screening test agents, for example, in 96-well plates.

An astrocyte culture may be prepared using methods known in the art using astrocytes that promote degeneration.

In a first set of non-limiting embodiments, an astrocyte culture may be prepared by the following method. An astrocyte cell suspension may be plated in glial medium (Dubelco Modified Eagle's medium (DMEM; Invitrogen, Carlsbad, Calif.) containing 10% fetal bovine serum (FBS; Invitrogen), 100 U/mL penicillin and 100 μg/mL streptomycin (penicillin/streptomycin, Invitrogen). After a time period such that greater than 80 percent and preferably greater than 90 percent of the cells are glial acidic fibrillary protein (GFAP)+ astrocytes (e.g., about 2 weeks), residual microglia may be eliminated by agitating the flasks (200 rpm; 6 h), after which astrocytes may be detached by 0.25% trypsin (Invitrogen) and plated onto coverslips, for example at a density of 20,000 cells/cm².

In a second set of non-limiting embodiments, where human astrocyte cultures are to be prepared, a protocol substantially as described by de Groot et al., [65] may be followed. In particular, resected tissue samples from brain or spinal cord may be collected in DMEM/HAMF10 (1:1) medium (Gibco) containing gentamycin (50 μg/ml) and kept at 4° C. until use. Prior to cell isolation, meninges and visible blood vessels should be removed, and tissues may be minced into ~2 mm3 cubes. A suspension of dissociated cells may be obtained from the tissue fragments after incubation at 37° C. for 20 min in Hank's balanced salt solution (HBSS) containing 2.5 mg/ml trypsin (T-0646; Sigma Chemical Co., St. Louis, Mo.) 0.2 mg/ml EDTA, 1 mg/ml glucose, and 0.1 mg/ml bovine pancreatic DNase I (Boehringer Mannheim, Germany). After digestion, the cell suspensions may be gently triturated and washed with DMEM/HAMF10 medium containing 10% (w/v) FCS (Invitrogen), penicillin/streptomycin. Independent cultures may be established from each brain or spinal cord sample. To avoid contamination of the astrocyte cultures with meningeal and blood monocyte-derived macrophages, single cell suspensions may be plated into uncoated 75 cm2 tissue culture flasks and incubated at 37° C. in a humidified atmosphere of 5% CO2 and 95% air for 2 hr. This step allows monocytes/macrophages to adhere to the bottom of the flasks. Subsequently, 10 ml of the supernatant containing dissociated cells and myelin debris may be plated into 75 cm2 flasks previously coated with poly-L-lysine (15 μg/ml; Sigma). Flasks may be incubated at 37° C. in a humidified atmosphere of 5% CO2 and 95% air for 48 hr after which the culture medium may be changed so as to remove unattached cells and myelin debris. Subsequently, the culture medium may be changed once a week with fresh medium and the flasks will be examined under phase contrast. Gradually, increasing colonies of proliferating cells may be detected (usually after 2 or 3 weeks in vitro). To eliminate residual microglia, 2-week-old flasks may be processed by agitating the flasks (200 rpm; 6 h), after which astrocytes may be detached by 0.25% trypsin (Invitrogen) and plated onto coverslips (density of 20,000 cells/cm2).

Motor neurons may be differentiated from stem cells using techniques known in the art. See, for example, [13, 67, 68]. Primary motor neurons may be prepared from a subject and put into culture using techniques known in the art. See, for example, [12].

In one specific non-limiting example, stem cells may be differentiated into motor neurons as follows. Embryonic stem cells may be induced to form embryonic bodies by growing the cells for 2 days in 1:1 (vol:vol) DMEM/Ham's F-12 medium (Invitrogen) containing B27 supplement (Invitrogen), penicillin/streptomycin and 0.1 mM 2-mercaptoethanol. To induce motor neuron differentiation, cultures of the resulting embryonic bodies may be treated with 1 μM retinoic acid and 400 nM sonic hedgehog agonist (e.g., Hh-Ag1.3, Curis Inc.) for five days, and then the cells may be dissociated with papain and plated at about 1600 cells per square centimeter in motor neuron medium, which is neurobasal medium (Invitrogen) containing 2% heat inactivated horse serum, B27 supplement, 0.5 mM glutamine, 25 μM 2-mercaptoethanol, and penicillin/streptomycin.

Where a degeneration-promoting astrocyte carries an SOD1 mutation, the SOD1 mutation may be any such mutation known in the art, including, but not limited to, mutations referred to in [3, 4, 5, 40-50]. For example, but not by way of limitation, an SOD1 mutation in the SOD1 gene may be one or more of a glycine-to-alanine substitution at position 93 (G93A), a glycine-to-cysteine substitution at position 93 (G93C), a glycine-to-arginine substitution at position 37 (G37R), a glycine-to-arginine substitution at position 85 (G85R), a leucine-to-valine substitution at position 106 (L106V), an isoleucine-to-threonine substitution at position 113 (I113T), a glutamic acid-to-glycine substitution at position 100 (E100G), a histidine-to-arginine substitution at position 43 (H43R), a glycine-to-serine or glycine-to-aspartic acid substitution at position 41 (G41S or G41D), or a leucine-to-valine substitution at position 38 (L38V).

Where a degeneration-promoting astrocyte carries an SMN mutation, the mutation(s) may be any such mutation(s) known in the art, including, but not limited to, those described in [54-64]. As specific, non-limiting examples, the SMN mutation may be SMN2 and/or SMN1 gene.

5.3 Assay Methods

The present invention provides for methods for identifying an agent useful in treating a neurodegenerative condition, comprising:
(i) establishing a culture system comprising (a) a neuron of the type afflicted in the neurodegenerative condition and (b) a component which promotes the degeneration of said neuron (e.g., a degeneration-promoting astrocyte or culture supernatant obtained therefrom);
(ii) adding a test agent to the culture system; and
(iii) evaluating whether the neuron in the culture system degenerates in the presence of test agent (e.g., relative to a control culture to which test agent has not been added);
wherein the ability of test agent to prevent or reduce degeneration of the neuron indicates that the test agent is useful in treating a neurodegenerative condition.

In particular, non-limiting embodiments, the present invention provides for methods for identifying an agent useful in treating ALS, comprising:
(i) establishing a culture system comprising (a) a motor neuron and (b) a component which promotes the degeneration of said motor neuron (e.g., a degeneration-promoting astrocyte (e.g., an astrocyte carrying a SOD1 mutation or obtained from an individual suffering from sporadic or familial ALS) or culture supernatant obtained therefrom);
(ii) adding a test agent to the culture; and
(iii) evaluating whether the motor neuron in the culture system degenerates in the presence of test agent (e.g., relative to a control culture to which test agent has not been added);
wherein the ability of test agent to prevent or reduce degeneration of the motor neuron indicates that the test agent is useful in treating ALS.

In particular, non-limiting embodiments, the present invention provides for methods for identifying an agent useful in treating SMA, comprising:
(i) establishing a culture system comprising (a) a motor neuron and (b) a component which promotes the degeneration of said motor neuron (e.g., a degeneration-promoting astrocyte (e.g., an astrocyte carrying a SMN mutation or obtained from an individual suffering from SMA) or culture supernatant obtained therefrom);

(ii) adding a test agent to the culture; and
(iii) evaluating whether the motor neuron in the culture system degenerates in the presence of test agent (e.g., relative to a control culture to which test agent has not been added);

wherein the ability of test agent to prevent or reduce degeneration of the motor neuron indicates that the test agent is useful in treating SMA.

In the foregoing, "treating" means resulting in inhibiting the progress of neurodegeneration, for example, but not by limitation, by one or more of the following: delaying the progression of the disease; reducing the severity of impairment; reducing the signs and/or symptoms associated with the condition; increasing survival, improving performance/function, prolonging survival; or increasing patient comfort. Where an assay "indicates that the test agent is useful in treating" a condition, further experimentation, such as animal studies and human clinical trials, as are conventionally required, would be warranted to confirm the activity observed in the assay.

The culture systems of the invention may be amenable to screening multiple test agents in parallel; for example, parallel cultures may be established in multi-well (e.g., 96-well) culture plates. In one specific, non-limiting embodiment of the invention, the screening may be performed by a Flash Cytometer® (Trophos SA, Marseille, France).

A test agent may be added to the culture system of the invention, and the extent of degeneration, apoptosis, or death of the neuron of interest may be evaluated relative to a control culture in which no test agent has been added (but otherwise essentially the same conditions are maintained). For example, where there is a fluorescent marker of viability, the level of fluorescence may be measured. Where the control culture manifests a decrease in a marker of degeneration, the ability of a test agent to reduce the extent of such decrease (or produce an increase) in the marker indicates that the test agent may be useful in preventing or reducing or treating degeneration. Where the control culture manifests an increase in a marker of apoptosis or cell death, the ability of a test agent to inhibit or reduce said increase (or produce a decrease) in the marker indicates that the test agent may be useful in preventing or reducing or treating degeneration. An example of a test agent which inhibited apoptosis of motor neurons is V5, as discussed in the example section below.

The time period for culturing prior to addition of test agent may be selected such that a control culture, lacking a test agent, may exhibit cell degeneration. For example, but not by way of limitation, the time period prior to adding test agent may be at least about 2 days, at least about 3 days, at least about 4 days, at least about 5 days, at least about 6 days, at least about 7 days, at least about 10 days, or at least about 2 weeks. The time period for culturing after adding test agent to the culture, preferably during which test agent is maintained in the culture, may be, for example and not by way of limitation, at least about 6 hours, at least about 12 hours, at least about 1 day, at least about 2 days, at least about 3 days, at least about 4 days, at least about 5 days, at least about 6 days, at least about 7 days, at least about 10 days, or at least about 2 weeks.

The following are non-limiting examples of a co-culture system which may be used to model ALS. Cultures as set forth below may be established in parallel as set forth above and used to screen multiple test agents to identify agents that inhibit motor neuron degeneration. The contents of the working examples are hereby incorporated into the detailed description of the invention.

6. EXAMPLE 1

Mutations in superoxide dismutase-1 (SOD1) cause a form of the fatal paralytic disorder amyotrophic lateral sclerosis (ALS), presumably by a combination of cell autonomous and non-cell autonomous processes. Here, we show that expression of mutant SOD1 in primary spinal motor neurons does not provoke motor neuron degeneration. Conversely, astrocytes expressing mutant SOD1 kill spinal primary and embryonic stem cell-derived motor neurons. This is triggered by soluble toxic factor(s) via a Bax-dependent mechanism. However, mutant astrocytes do not cause the death of spinal GABAergic or dorsal root ganglion neurons or embryonic stem cell-derived interneurons. In contrast to astrocytes, fibroblasts, microglia, cortical neurons, and myocytes expressing mutant SOD1 do not cause overt neurotoxicity. These findings indicate that astrocytes may play a role in the specific degeneration of spinal motor neurons in ALS. Identification of the astrocyte-derived soluble factor(s) may have far-reaching implications for ALS from both a pathogenic and therapeutic standpoint.

Astrocytes are the most abundant non-neuronal cells in the central nervous system, and their implication in neurodegenerative processes become increasingly appreciated[5, 10, 11]. To determine the role of astrocytes in neurodegeneration in the mutant SOD1 ALS mouse model, we used co-cultures composed of astrocyte monolayer (AML) and primary spinal (pMN) or embryonic stem cell-derived (ESMN) motor neurons. This co-culture system showed that while mutant SOD1 expression in pMN caused neuronal morphometric alterations, its expression in astrocytes affected both morphometry and survival of pMN and ESMN. We also found that these deleterious effects were: (i) mediated by a soluble factor; (ii) recapitulated the selectivity of ALS neurodegeneration since mutant astrocytes were toxic to pMN and ESMN but not to dorsal root ganglion (DRG) neurons or spinal primary GABAergic or embryonic stem cell-derived interneurons; (iii) specific to astrocytes since other cell types including microglia expressing mutant SOD1 failed to induce overt motor neuron degeneration; and (iv) abrogated by a soluble inhibitor of the pro-cell death protein Bax. Our data provide evidence that astrocytes are specific contributors to spinal motor neuron degeneration in mutant SOD1-linked ALS.

6.1 Materials and Methods

Procedures using laboratory animals were in accordance with the US National Institutes of Health guidelines for the use of live animals and approved by Institutional Animal Care and Use Committee of Columbia University.

Primary Astrocyte Culture.

Glial monolayers were prepared from spinal cord from transgenic $SOD^{G93A}$, $SOD^{G37R}$, $SOD^{G85R}$, $SOD^{WT}$ of newborn pups as described by Silva and collaborators[31]. Cell suspensions were plated in glial medium: Dubelco Modified Eagle's medium (DMEM; Invitrogen, Carlsbad, Calif.) containing 10% fetal bovine serum (FBS; Invitrogen), 100 U/mL penicillin and 100 µg/mL streptomycin (penicillin/streptomycin, Invitrogen). After 2 weeks, glial cultures contained 95% of glial acidic fibrillary protein (GFAP)+ astrocytes, 5% of CD11b+ microglia, and no neuron or oligodendrocyte as indicated by the lack of respectively MAP2 or 2'-3'-cyclic nucleotide phosphohydrolase immunoreactivity (data not shown). To eliminate residual microglia, 2-week-old flasks were agitated (200 rpm; 6 h) and astrocytes were detached by 0.25% trypsin (Invitrogen) and plated onto coverslips at a density of 20,000 cells/cm$^2$.

Embryonic Stem Cell-Derived Neuron Cultures.

Cells were derived from Hlxb9-GFP1Tmj transgenic mice[13] and differentiated into ESMN as described previously[13]. To form EBs, cells were grown for 2 d in 1:1 (v/v) DMEM/Ham's F-12 media (Invitrogen) medium containing B27 supplement (Invitrogen), penicillin/streptomycin and 0.1 mM β-mercaptoethanol (Sigma, Saint Louis, Mo.). They were treated with 1 µM retinoic acid (Sigma) and 400 nM sonic hedgehog agonist (Hh-Ag1.3, Curls Inc., Cambridge, Mass.) for 5 d and dissociated with papain (Worthington, Lakewood, N.J.). Cells were plated at 1,600 eGFP-positive cells/cm$^2$ in motor neuron medium: Neurobasal medium (Invitrogen) containing 2% horse serum (heat inactivated; Invitrogen), B27 supplement, 0.5 mM glutamine (Invitrogen), 25 µM β-mercaptoethanol, penicillin/streptomycin. To obtain LH2-positive neurons, once EBs were formed they were treated with 0.1 µM retinoic acid and 15 ng/mL bone morphogenetic protein 4 (R&D systems, Minneapolis, Minn.) for 5 d before papain dissociation. Then, 1,500 cells/cm$^2$ were plated onto astrocyte monolayer in motor neuron medium.

Primary Neuronal Cultures.

Spinal neuronal cultures were done as previously described[12] from E12.5 Hlxb9-GFP1Tmj transgenic, wild-type or transgenic SOD$^{G93A}$, SOD$^{G37R}$, SOD$^{G85R}$, SOD$^{WT}$ rodents. Cells were plated at 1500 eGFP$^+$ cells/cm$^2$ for Hlxb9::eGFP and at 5000 cells/cm$^2$ for the other cultures. The plating was done either on 0.01% poly-D-lysine and 10 µg/mL laminin (poly-D-lysine/laminin) coated coverslips or on astrocyte monolayers containing either motor neuron medium (above) supplemented with a cocktail of trophic factors composed of 0.5 ng/mL glia-derived neurotrophic factor, 1 ng/mL brain-derived neurotrophic factor (BDNF), and 10 ng/mL ciliary neurotrophic factor (trophic factor cocktail, R&D systems) or astrocyte-conditioned motor neuron medium (see next section).

DRG cultures were prepared as previously described[32,33]. Cell suspensions were plated at 1,500 cells/cm$^2$ onto poly-D-lysine/laminin coated coversilps in motor neuron medium conditioned for 1 week by the different astrocyte monolayers (see below) and supplemented with 10 ng/mL of neurotrophin-3 and nerve growth factor (R&D systems).

Cortical neuron cultures were prepared as previously described by Rideout and collaborators[34] from E17.5 mouse brains. Neurons were plated in neurobasal medium supplemented with B27, 0.5 mM glutamine and penicillin/streptomycin onto poly-D-lysine/laminin coated dishes.

Primary Non-Neuronal Cultures.

Microglia was collected from glial monolayer as described above and centrifuged (500×g, 5 min). Cells were resuspended in fresh glial medium and plated at 40,000 cells/cm$^2$. Fibroblasts were obtained as described previously by Kaji and collaborators[35] and plated onto dishes in minimum essential medium (Invitrogen) containing 10% FBS, and penicillin/streptomycin. Myoblast were obtained from rat pup skin after digestion with dispase/collagenase IV (37° C., 25 min; Worthington). Cells were suspended in growth medium (Hams F-10 medium (Invitrogen) supplemented with 15% horse serum, penicillin/streptomycin and 5 ng/mL β-fibroblast growth factor (R&D systems) and plated on collagen-coated dishes. At 90% of confluency, cells were differentiated with 6 µg/mL insulin and cultured in Hams F-10 medium supplemented with 1.5% horse serum and penicillin/streptomycin. Myotubes formed in 2-3 d.

Conditioned Medium Preparation.

Cultures of astrocytes, microglial, fibroblasts and muscle were prepared from both wild-type and transgenic SOD1$^{G93A}$ rodents. Once confluency or differentiation was reached, their culture media were replaced with either motor neuron or DRG medium. After 7 d, conditioned media were collected and centrifuged (500×g, 10 min) to eliminate floating cells. Supernatants were collected and frozen. Before use, conditioned media were supplemented with 4.5 g/mL D-glucose (final concentration), penicillin/streptomycin and the cocktail of trophic factors and filtered.

Immunocytochemistry and Cell Labeling.

For EthD (Molecular Probes) estimation of death, cells were incubated with 2 µM EthD (diluted in D-PBS; 45 min; RT) as we previously reported[36]. For immunocytochemistry and the other cell labelings, cells were processed as we previously described[36]. Primary antibodies used were: rabbit polyclonal anti-eGFP (1:2000; Molecular Probes), anti-fractin (1:5000; BD Pharmingen, San Jose, Calif.), GABA (1:2000; Chemicon), anti-Lim2 (1:150; from Dr. Jessell's lab), and anti-HB9 (1:1000 from T M Jessell's lab); goat polyclonal anti-ChAT (1:100; Chemicon, Temecula, Calif.); sheep polyclonal anti-SOD1 (1:500; Calbiochem), rabbit anti-protein gene product 9.5 (PG-P 9.5; 1:2000; Chemicon) and mouse monoclonal anti-MAP-2 (1:1000; Chemicon), anti-GFAP (1:1000; Sigma), anti-Islet 1/2 (1:100; from TM Jessell's lab), anti-LH2 (1:2; from T M Jessell's lab), and anti-SMI-32 for non-phosphorylated neurofilament heavy chain (1:1000, Sternberger monoclonals, Lutherville, Md.). Terminal deoxy-UTP nick-end labeling (Tunel, in situ cell death detection kit, Roche Diagnostic, Indianapolis, Ind.) were performed following the manufacturer's recommendations.

Pharmacological Treatments.

zVAD-fmk and V5 (Sigma) were dissolved in DMSO and add to co-cultures to final concentrations ranging from 10-20 µM for the former and 50-200 µM for the latter. Fresh drugs were added daily. Cell survival and death were evaluated at 7 d by counting eGFP$^+$/HB9$^+$ neurons, and EthD- and fractin-labeled cells as described below.

Morphometric Analysis.

For estimation of motor neuron morphometric parameters, images were captured at ×50 under fluorescent examination using Axiovision LE Rel. 4.2 software (Zeiss) and soma diameter and length distance between two points for axon length were measured.

Cell Counting and Statistics.

Results are expressed as mean±standard error of the mean (s.e.m.) for 3-6 independent experiments. Each experiment corresponds ≥3 transgenic and non-transgenic co-cultures from the same litter and 3 coverslips per time point and per condition. Each coverslip was counted at ×100 under fluorescent examination in its entirety. To determine the proportion of dying or apoptotic neurons, ≥750 MAP2$^+$ neurons were counted per culture. Differences between means were analyzed by a two-tailed Student's t-test whereas among means by one- or two-way ANOVA with the different types of mice, treatment doses, or time as the independent factors. When ANOVA showed significant differences, pair-wise comparisons between means were tested by Newman-Keuls post-hoc testing. All of these statistical analyses were performed using SigmaStat for Windows (version 3.1; Jandel Corp., San Rafael, Calif.). For morphometry studies, differences were analyzed by Kolmogorov-Smirnov test (www-.physics.csbsju.edu/stats/KS-test.n.plot_form.html). In all analyses, the null hypothesis was rejected at the 0.05 level.

6.2 Results

Primary and Embryonic Stem Cell-Derived Cultures are Complementary Systems.

We used cultures motor neuron derived from: (i) mouse embryonic spinal cord, as pMN have been shown to be suitable for probing the molecular basis of selective motor neuron degeneration caused by mutant SOD1[12]; and, (ii) mouse embryonic bodies (EBs), as ESMN not only exhibit many of the molecular markers and functional properties of spinal motor neuron[13, 14] but also have the unique characteristic of being readily expandable.

pMN were obtained from E12.5 embryonic mouse spinal cords and yielded multipolar motor neuron immunopositive for microtubule-associated proteins 2 (MAP2), for the motor neuron specific transcription factor HB9, and for non-phosphorylated neurofilament (FIG. 1$a,b$). This method was used to produce pMN from transgenic mouse embryos expressing either SOD1$^{G93A}$, SOD1$^{G85R}$, or SOD1$^{G37R}$ ($^{G93A,\ G85R\ or\ G37R}$pMN)—the three most characterized mouse models of ALS[3-5]—as well as from their non-transgenic littermates ($^{NTg}$pMN). pMN were also prepared from transgenic embryos expressing human wild-type SOD1 ($^{WT}$pMN). To facilitate the identification of motor neuron, transgenic Hlxb9-GFP1Tmj mouse embryos expressing enhanced green fluorescent protein ($^{eGFP}$pMN) under the control of the HB9 promotor[13] were also used. eGFP-generated fluorescence was observed in both cell bodies and processes of large MAP2$^+$ neurons which colocalized with the cholinergic transmitter synthetic enzyme choline acetyltransferase (ChAT) (FIG. 1$c,d$).

ESMN were generated from stem cells derived from the transgenic Hlxb9-GFP1Tmj embryos[13]. This culture system typically contained ~30% eGFP$^+$ neurons (FIG. 1$e$). All of these neurons expressed MAP2 (FIG. 1$e,f$) and were immunoreactive for both ChAT and the LIM homeodomain proteins Isl 1/2 (FIG. 1$g,h$), confirming their motor neuron phenotype.

Similar Survival of NTg, SOD1$^{WT}$ and Mutant SOD1-Expressing Motor Neurons.

To first examine whether expression of mutant SOD1 promotes the degeneration of spinal motor neuron, $^{G93A,\ G37R,\ G85R,\ WT}$ were $^{NTg}$pMN were plated on $^{NTg}$AML. All transgenic and non-transgenic cultures were plated at the same density of neurons (see Materials and Methods), and resulted in the same number of pMN one d after plating (FIG. 2$a$). Thereafter, the number of surviving $^{G37R,\ WT}$ and $^{NTg}$pMN declined by ~25% over 14 d without any genotypic difference (FIG. 2$a$). The absence of genotypic effect could not be attributed to a loss of mutant SOD1 expression in transgenic neurons[15], since its level did not change during the course of the experiments (FIG. 7$a$-$e$).

Mutant SOD1-Expressing Motor Neurons Exhibit a Cell Autonomous Phenotype.

Contrasting the lack of difference in pMN number among the genotypes ($F_{[2,\ 10]}=0.47$, $p=0.64$), both at one (not shown) and 14 d in culture, $^{G37R}$pMN cell body diameters were 19% smaller (Kolmogorov-Smimov test; $p<0.001$) than those of $^{WT}$ and $^{NTg}$pMN (FIG. 2$b$). Likewise, $^{G37R}$pMN had a strikingly lower frequency of axons ≥700 μm compared to $^{WT}$ and $^{NTg}$pMN (FIG. 2$c$). Similar results were obtained with $^{G93A}$ and $^{G85R}$ pMN. Thus, these findings demonstrate that, under the present experimental conditions, expression of mutant SOD1 in motor neuron caused a mild cell-autonomous abnormal phenotype.

Mutant SOD1-Expressing Astrocytes Alter Motor Neuron Morphometry.

We then asked whether the above neuronal morphometric abnormalities caused by mutant SOD1 result from a cell-autonomous mechanism. We plated $^{NTg}$pMN and ESMN on $^{G93A}$ and $^{NTg}$AML. At 14 d post-plating, $^{NTg}$pMN grown on $^{G93A}$AML exhibited the same morphometric alterations as $^{G37R,\ G85R,}$ and $^{G93A}$pMN grown on $^{NTg}$AML. Similarly, at 3 and 7 d post-plating, ESMN grown on $^{G93A}$AML exhibited reduced axonal lengths and cell body diameters compared to ESMN grown on $^{NTg}$AML (FIG. 3$a,b$).

Astrocytes Expressing Mutant SOD1 Affect Motor Neuron Survival.

Because the neuronal morphometric alterations could be recapitulated through a non-cell autonomous process, we then asked whether the expression of mutant SOD1 in astrocytes could also produce more profound neuronal damage. Here, $^{eGFP}$pMN and ESMN were initially plated on $^{G93A}$ and $^{NTg}$AML from rats[16] to increase the yield of glial monolayers. The numbers of $^{eGFP}$pMN plated on $^{NTg}$AML decreased by ~25% over 14 d (FIG. 3$c$). Under the same conditions, 70-80% of the 1,076±19 ESMN counted at d 1 were lost over the next four d; thereafter, the loss of ESMN slowed, decaying at a rate reminiscent of that of pMN. Because of the pronounced death of ESMN in co-cultures composed of astrocytes of both genotypes, the numbers of ESMN plated on $^{G93A}$AML were normalized to those plated on $^{NTg}$AML (FIG. 3$e$). Following this data transformation, both pMN and ESMN values could be compared (FIG. 3$c,e$). This analysis revealed that the loss of both $^{eGFP}$pMN ($F_{[3,\ 37]}=6.3$, $P=0.0015$) and ESMN ($F_{2,\ 24}=6.0$, $P=0.003$) were more profound when grown on $^{G93A}$AML compared to $^{NTg}$AML.

Similar results were obtained if, instead of rat, mouse $^{G93A}$AML or if instead of $^{eGFP}$pMN, $^{NTg}$pMN were used at seeding densities varying from 1,000 to 10,000 per dish (FIG. 8$a$). Furthermore, $^{G37R}$ or $^{G85R}$AML caused comparable toxicity to $^{eGFP}$pMN or ESMN as $^{G93A}$AML (FIG. 3$d,f$). In contrast, the effect of $^{WT}$AML on the survival of $^{eGFP}$pMN or ESMN did not differ from that of $^{NTg}$AML (FIG. 3$d,f$), ruling out the possibility that the toxicity of mutant AML to pMN and ESMN was merely due to SOD1 overexpression. These results show that expression of mutant SOD1 in astrocytes represents a toxic pathway, which is in keeping with a non-cell-autonomous mechanism in ALS pathogenesis.

Mutant Astrocytes Affect Equally Wild-Type and Mutant SOD1 Motor Neurons.

We then asked whether the combination of mutant motor neuron grown on mutant astrocytes would give rise to a more severe neurodegenerative phenotype than any other co-culture combination. Although at d 1 the numbers of pMN were identical among the different co-culture combinations (FIG. 3$g$), at d 7 and 14, there were significantly fewer surviving pMN of either genotype when cultured on $^{G93A}$AML compared to $^{NTg}$AML (FIG. 3$g$). However, none of these time points showed a loss of $^{G37R}$pMN different (Newman-Keuls, $p>0.3$) from that of $^{NTg}$pMN grown on $^{G93A}$AML (FIG. 2$f$). Likewise, the morphometric alterations of $^{G37R}$pMN did not differ from those of $^{NTg}$pMN grown on $^{G93A}$AML (FIG. 9$a,b$). In addition, at d 7, transgenic pMN expressing different SOD1 mutants and grown on $^{G93A}$AML were identically affected (FIG. 8$b$). Conversely, high expression of human SOD1$^{WT}$ in pMN appeared to attenuate $^{G93A}$AML-mediated toxicity (FIG. 8$b$). Thus, these data indicate that expression of mutant SOD1 in both astrocytes and motor neuron did not exacerbate the death or the morphometric changes of pMN caused by the mutant SOD1-expressing astrocytes only.

Mutant Astrocytes Mediate Motor Neuron Death Through a Soluble Mechanism.

To determine whether the effect of mutant astrocytes on pMN and ESMN is caused by a soluble factor, $^{eGFP}$pMN were plated onto poly-D-lysine/laminin-coated coverslips and cultured for 7 d with media preconditioned by either $^{G93A}$ or $^{NTg}$AML (FIG. 4). Astrocyte conditioned media (CMd), were frozen until assay and re-supplemented before use with glucose and trophic factors (see Method section). This showed that the numbers of $^{eGFP}$pMN exposed to $^{G93A}$CMd were significantly lower (Newman-Keuls, p<0.01) than those of $^{eGFP}$pMN exposed to $^{NTg}$ or $^{WT}$CMd (FIG. 4a). These observations support that mutant astrocytes exert toxicity to motor neurons through the release of a soluble factor. This putative toxic mediator appeared specific to astrocytes since media conditioned in the same manner with primary skeletal myocytes, spinal cord microglia, cerebral cortex neurons, or skin fibroblasts expressing comparable levels of SOD1$^{G93A}$ failed to cause comparable reductions in $^{eGFP}$pMN and ESMN counts (FIG. 4b,c).

Mutant SOD1 Astrocyte Toxic Effect is Specific to Motor Neurons.

To determine whether the observed astrocyte toxicity is specific to motor neurons, we evaluated the fate of primary spinal GABAergic or DRG neurons (FIG. 5a-d) and non-motor neuron embryonic stem cell-derived neurons such as eGFP$^-$/MAP2$^+$ neurons or Lim1/2$^+$ D3 and LH2$^+$ D1 interneurons (FIG. 5e-h).

By d 7, unlike $^{eGFP}$pMN, the numbers of GABAergic (FIG. 5a,b) and DRG neurons (FIG. 5c,d) respectively plated on $^{G93A}$AML or exposed to $^{G93A}$CMd were unchanged as compared to those on $^{NTg}$AML or in $^{NTg}$CMd. Similarly, neither soma diameter nor axonal length of GABAergic interneurons plated on $^{G93A}$AML differed from that of their counterparts plated on $^{NTg}$AML (FIG. 10a,b).

In our embryonic stem cell/astrocyte co-cultures, one d after plating, in addition to ESMN, we found 54% (i.e., 1094±36) of eGFP$^-$/MAP2$^+$ neurons of which 15% (i.e., 312±26) are Lim1/2$^+$ D3 interneurons (FIG. 5e,f). In contrast with ESMN, neither the numbers of eGFP$^-$/HB9$^-$/MAP2$^+$ nor those of eGFP$^-$/Lim1/2$^+$ differed between co-cultures made of $^{G93A}$ and $^{NTg}$AML over 14 d (FIG. 5f). Next, we subjected EBs to a modified protocol of differentiation giving rise to 70% of D1 interneurons expressing Lhx2/Lhx9 transcription factors (recognized by the LH2 antibody)[17] out of the total Map2$^+$ neuronal population (FIG. 5g). Confirming further the selectivity of mutant astrocyte toxicity for the motor neuron phenotype, the number of eGFP$^-$/LH2$^+$ interneurons was similar between co-cultures made of $^{G93A}$ and $^{NTg}$AML, at both 2 and 7 d post plating (FIG. 5h). Thus, these results suggest that motor neuron identity confers susceptibility to mutant astrocyte-mediated toxicity.

Astrocyte-Induced Motor Neuron Death Depends on Bax.

To confirm that the differences in the number of ESMN reflected differences in cell survival, we compared the proportion of dying neurons between the two co-culture genotypes using the DNA dye ethidium homodimer (EthD), which selectively permeates the broken membranes of dying cells. The percentage of EthD-labeled embryonic stem cell-derived MAP2$^+$ neurons at 7 d was 1.34-fold higher in co-cultures composed of $^{G93A}$AML than in co-cultures composed of $^{NTg}$AML (FIG. 6c). To ask whether the depleted survival of ESMN reflected the activation of apoptotic pathway, we combined staining with the membrane permeant DNA dye Hoechst 33342 (FIG. 6a,b) and an antibody against fractin (FIG. 6a), which is a 32 kDa fragment of β-actin generated by activated caspase-3[18]. This showed that by 7 d, the percentage of fractin-immunostained cells with condensed nuclei was 1.51-fold higher in co-cultures composed of $^{G93A}$AML compared to those composed of $^{NTg}$AML (FIG. 6c). All cell nuclei with condensed chromatin evidenced by Hoechst 33342 were also positive for apoptotic DNA fragmentation as evidenced by terminal deoxy-UTP nick-end labeling (FIG. 6b).

To characterize the biochemical pathway activated in ESMN by mutant astrocyte, cultures were incubated with the membrane-permeable pentapeptide VPMLK (V5), which inhibits the death agonist Bax[19]. This treatment reduced specifically the numbers of fractin-positive cells in co-culture composed of $^{G93A}$AML (FIG. 6c). In addition, V5 diminished the numbers of EthD-labeled cells specifically in co-culture composed of $^{G93A}$AML (FIG. 6d) and augmented the numbers of surviving ESMN plated on $^{G93A}$AML (FIG. 6e). Thus, the present results indicate that the soluble factors produced by mutant astrocytes kill ESMN through the activation of a Bax-dependent cell death pathway.

6.3 Discussion

A role for non-neuronal cells in the demise of neighboring motor neuron in familial ALS caused by SOD1 mutations is increasingly recognized, and the underpinning of this non-cell autonomous pathogenic element is just beginning to be uncovered. Our use of a neuronal/glial co-culture system provides evidence that astrocytes expressing either catalytically active or inactive mutant SOD1 cause death of wild-type pMN and ESMN (FIG. 3). While mutant astrocytes kill wild-type motor neurons, they do not affect the survival of DRG neurons or spinal interneurons. This toxic effect is mediated through the release of soluble factor(s) from astrocytes and culminates in the recruitment of a Bax-dependent death machinery within motor neurons. In contrast, mutant microglia or mutant cortical neurons, fibroblasts, or myocytes exert minimal or no effect on motor neuron survival (FIG. 4). The present findings indicate that this neurotoxicity is produced by a specific interaction between astrocytes and motor neurons, in that, among a variety of non-neuronal cell types, astrocytes are the only ones found to be endowed with a potent toxic property, and, among a variety of neuronal subtypes, motor neurons are the only ones found to succumb to this astrocyte-induced toxicity. Thus, our data suggest that astrocytes play a specific role in spinal motor neuron degeneration in ALS.

Given these data, we conclude that, in spinal cords of chimeric mice[6], among mutant non-neuronal cells, astrocytes can contribute to the transmission of the pathological phenotype to wild-type motor neurons. However, transgenic mice expressing mutant SOD1, driven by the astrocyte specific promoter GFAP, have generated a more subtle phenotype characterized by gliosis but no overt motor neuron degeneration[21]. Without knowing the proportion of astrocytes expressing mutant SOD1 or the level of expression of this toxic protein per astrocyte, one cannot exclude that the amount of astrocytic mutant SOD1 in the spinal cord might not have been sufficient enough to cause motor neuron degeneration in these transgenic mice. Furthermore, precedent exists for the ability of mutant protein-expressing astrocytes to induce neurodegeneration in vivo. Indeed, it has been shown that expression of mutant ataxin-7 in astrocytes causes degeneration of wild-type Purkinje cells in a mouse model of spinocerebellar atrophy[10].

While our data implicate astrocytes in mutant SOD1-induced neurotoxicity, they do not preclude a role for other cell types in the disease process. The emergence of the ALS phenotype can be retarded by decreasing the expression of mutant SOD1 selectively in motor neurons of transgenic mutant SOD1 mice[8, 15]. Also relevant to this idea is the demonstration that transgenic mice engineered to express the highest levels of mutant SOD1 in both neurons and astrocytes do develop an ALS phenotype[22]. Although our data show that mutant SOD1 expressed in pMN did not kill spinal pMN by 14 d in culture, Di Giorgio, Carrasco and collaborators[20] did find that survival of ESMN expressing SOD1$^{G93A}$ is reduced compared to their wild-type counterparts when cultured for more than 14 d. Thus, mutant SOD1 in astrocytes and, apparently in a more protracted manner, in motor neurons, may act in concert to kill spinal motor neurons. Deletion of mutant SOD1 in microglia[8] or the absence of microglia expressing mutant SOD1[7] also prolonged survival in transgenic mutant SOD1 mice, but without delaying the age at onset of symptoms. Furthermore, mutant SOD1 microglia did not induce the death of wild-type motor neurons either in vitro (present work) or in vivo[7]. These results suggest that microglial expression of mutant SOD1 alters disease duration, but does not induce neurodegeneration in this ALS model. They also suggest that among glial cells, both microglia and astrocytes contribute to the ALS phenotype by playing complementary roles in the disease process.

Although this work focuses on neuronal death, we also examined morphometric parameters and found that mutant SOD1 pMN had smaller cell bodies and shorter axons compared to their wild-type counterparts (FIG. 2). We show, however, that these mild morphological alterations could be reproduced non-cell autonomously and, apparently, they were not exacerbated by having mutant SOD1 expressed in both pMN and astrocyte. While the molecular basis of these morphometric changes remains to be determined, they may reflect abnormalities specific to motor neurons, since under similar experimental conditions, they were not observed in GABAergic interneurons. Under the various co-culture combinations, the morphological alterations occurred prior to or in the absence of detectable pMN death, and in the absence of neuromuscular junctions, suggesting that they represent early abnormalities initiated within the motor neurons. Such early neuromuscular junction-independent change is reminiscent of the aberrant hyperexcitability[23] and Na$^+$-channel dysfunction seen in mutant SOD1 motor neurons[24]. One interesting possibility is that these morphological and electrophysiological perturbations represent different manifestations of a common pathogenic mechanism in motor neurons.

As for the molecular basis of this astrocyte non-cell autonomous toxicity to spinal motor neurons, the pan-caspase inhibitor zVAD-fmk (FIG. 12a-c) or the inhibitor of soluble Fas ligand, Fas:Fc (FIG. 11a-e) or neutralizing antibodies against nerve growth factor—which were all shown to attenuate apoptosis in cultured motor neurons[12, 25]—failed to improve survival of ESMN. In contrast, Bax inhibition provided striking protection specifically against astrocyte-mediated motor neuron death (FIG. 6). This result is consistent with the in vivo demonstration that Bax ablation completely prevents the loss of spinal motor neurons in transgenic mutant SOD1 mice[26]. However, Bax deletion did little on the lifespan of transgenic mutant SOD1 mice[26], suggesting that pathways other than Bax may also contribute to the motor neuron damage in vivo and, possibly, in our cell culture system. Our experiments with conditioned media (FIG. 4) indicate that mutant astrocytes produce soluble molecule(s) which impair motor neuron survival. Studies of Huntington's disease[27] and spinocerebellar atrophy[10] have implicated neuronal excitotoxicity due to decreased glutamate uptake by mutant astrocytes as the basis of their non-cell autonomous properties. In ALS, a similar mechanism may operate since expression of the astrocytic EAAT2 glutamate transporter is reduced by 90% in the ventral horn of paralyzed transgenic SOD1$^{G93A}$ rats[28]. However, extracellular glutamate levels are not increased in our co-cultures from mutant SOD1 animals (FIG. 11a), glutamate uptake is not impaired in mutant astrocyte cultures (FIG. 11b) and a potent antagonist of AMPA (α-amino-3-hydroxy-5-methyl-4-isoxazolepropionic acid)/kainate receptors fails to prevent mutant astrocyte toxicity (FIG. 11c). Additionally, key toxic chemokines such as interleukin-1β, interleukin-6, interferon-γ, and tumor necrosis factor-α were either undetectable or similarly produced by wild-type and mutant astrocytes (FIG. 11e).

ESMN have emerged as a potential repair reagent for the treatment of spinal cord diseases such as ALS. However, our study and that of Di Giorgio, Carrasco and collaborators[20] show that mutant astrocytes impair the survival of wild-type ESMN. This fact implies that wild-type ESMN, upon engraftment into ALS spinal-cords, may be subjected to a hostile cellular environment challenging their ability to survive and to grow processes. Alternatively, embryonic stem cells may provide attractive prospects of therapies for ALS via avenues distinct from the mere replacement of motor neurons. Our demonstration that ESMN respond to mutant astrocyte-mediated toxicity like pMN suggests that ESMN offer an invaluable, readily expandable cellular tool for the high-throughput screening of small neuroprotective molecules in ALS. In addition, embryonic stem cells may also be differentiated into astrocytes[29]. In light of our data and those of Di Giorgio, Carrasco and collaborators[20], it is possible that grafting wild-type embryonic stem cell-derived astrocytes into ALS spinal cords may be useful for diluting the non-cell autonomous toxic phenotype, thereby attenuating the degeneration of neighboring motor neurons.

The identification of the toxic factor(s) responsible for the effects of mutant astrocytes on motor neuron survival represents an important challenge that may greatly benefit from new technologies like informatics-assisted protein profiling used by Lukas and collaborators in transgenic mutant SOD1 mice[30]. Once known, the toxic factors may provide new insights into the mechanism by which motor neuron die. This work may be relevant, not only to the rare familial form of ALS linked to mutant SOD1, but also to the common sporadic form of this incurable disease. Early diagnosis of ALS is difficult and often delayed by the insidious onset of symptoms that mimic other conditions, and clinical trials are slow in determining whether a treatment is efficacious. The discovery of astrocyte toxic mediators may thus lead to their use as biomarkers for the early diagnosis of ALS, to measure the progression of the disease, and to assess the effects of treatment as well as to develop new therapies aimed at mitigating motor neuron degeneration in ALS.

8. EXAMPLE 2

Miniaturization of the Co-Culture Model in 96 Well-Plates.

In order to develop an ALS cell-based model for high-throughput screening studies, the astrocyte/motor neuron (MNs) co-culture was adapted to a 96-well-plate format. Mouse embryonic stem-cell derived motor neurons (ES-MNs) and/or primary mouse MNs were seeded in 96-well plates in which half of the wells contained confluent wild-type astrocytes and half contained confluent mutant SOD1 astrocytes derived from rodent primary cultures or from mouse embryonic stem cells. The ES-MNs and/or primary MNs both express enhanced green fluorescent protein (GFP⁺) under the motor neuron-specific HB9 promoter. The plated MNs were monitored using the Flash Cytometer at 1, 5, 7, and 8 DIV. The GFP⁺ MN counts obtained using the software TINA showed that the survival of MNs grown on SOD1$^{G93A}$ astrocytes decreased over time to 55% of that of their counterparts grown on wild-type astrocytes by 7 DIV, and did not further decrease thereafter. Next, MNs were seeded on 96-well plates layered entirely with confluent SOD1$^{G93A}$ astrocytes. In reviewing the coefficient of variation (CV; SD/mean) per line and per column of five independent experiments, it was found that the mean CV is 8.5±0.3% at 1 DIV, confirming the efficiency of the plating technique. In parallel experiments, MNs cultured on poly-D-lysine/laminin coated 96-well plates were exposed to astrocyte conditioned media produced from both wild-type and SOD1$^{G93A}$ astrocytes. It was found that the survival of MNs exposed to SOD1$^{G93A}$ astrocyte conditioned medium decreased over time to 50% of that of their counterparts exposed to wild-type astrocyte conditioned mediums by 7 DIV.

8. REFERENCES

1. Rosen, D. R. et al. Mutations in Cu/Zn superoxide dismutase gene are associated with familial amyotrophic lateral sclerosis. *Nature* 362, 59-62 (1993).
2. Deng, H.-X. et al. Amyotrophic lateral sclerosis and structural defects in Cu, Zn superoxide dismutase. *Science* 261, 1047-1051 (1993).
3. Gurney, M. E. et al. Motor neuron degeneration in mice that express a human Cu, Zn superoxide dismutase mutation. *Science* 264, 1772-1775 (1994).
4. Wong, P. C. et al. An adverse property of a familial ALS-linked SOD1 mutation causes motor neuron disease characterized by vacuolar degeneration of mitochondria. *Neuron* 14, 1105-1116 (1995).
5. Bruijn, L. I. et al. ALS-linked SOD1 mutant G85R mediated damage to astrocytes and promotes rapidly progressive disease with SOD1-containing inclusions. *Neuron* 18, 327-338 (1997).
6. Clement, A. M. et al. Wild-Type Nonneuronal Cells Extend Survival of SOD1 Mutant Motor Neurons in ALS Mice. *Science* 302, 113-117 (2003).
7. Beers, D. R. et al. Wild-type microglia extend survival in PU.1 knockout mice with familial amyotrophic lateral sclerosis. *Proc. Natl Acad. Sci. USA* 103, 16021-16026 (2006).
8. Boillee, S. et al. Onset and Progression in Inherited ALS Determined by Motor Neurons and Microglia. *Science* 312, 1389-1392 (2006).
9. Kostic, V., Jackson-Lewis, V., De Bilbao, F., Dubois-Dauphin, M., & Przedborski, S. Bcl-2: Prolonging life in a transgenic mouse model of familial amyotrophic lateral sclerosis. *Science* 277, 559-562 (1997).
10. Custer, S. K. et al. Bergmann glia expression of polyglutamine-expanded ataxin-7 produces neurodegeneration by impairing glutamate transport. *Nat. Neurosci.* 9, 1302-1311 (2006).
11. Das, S. & Potter, H. Expression of the Alzheimer amyloid-promoting factor antichymotrypsin is induced in human astrocytes by IL-1. *Neuron* 14, 447-456 (1995).
12. Raoul, C. et al. Motoneuron Death Triggered by a Specific Pathway Downstream of Fas. Potentiation by ALS-Linked SOD1 Mutations. *Neuron* 35, 1067-1083 (2002).
13. Wichterle, H., Lieberam, I., Porter, J. A., & Jessell, T. M. Directed differentiation of embryonic stem cells into motor neurons. *Cell* 110, 385-397 (2002).
14. Miles, G. B. et al. Functional properties of motoneurons derived from mouse embryonic stem cells. *J. Neurosci.* 24, 7848-7858 (2004).
15. Raoul, C. et al. Lentiviral-mediated silencing of SOD1 through RNA interference retards disease onset and progression in a mouse model of ALS. *Nat. Med.* 11, 423-428 (2005).
16. Nagai, M. et al. Rats expressing human cytosolic copper-zinc superoxide dismutase transgenes with amyotrophic lateral sclerosis: associated mutations develop motor neuron disease. *J. Neurosci.* 21, 9246-9254 (2001).
17. Lee, K. J., Mendelsohn, M., & Jessell, T. M. Neuronal patterning by BMPs: a requirement for GDF7 in the generation of a discrete class of commissural interneurons in the mouse spinal cord. *Genes Dev.* 12, 3394-3407 (1998).
18. Suurmeijer, A. J., van der Wijk, J., van Veldhuisen, D. J., Yang, F., & Cole, G. M. Fractin immunostaining for the detection of apoptotic cells and apoptotic bodies in formalin-fixed and paraffin-embedded tissue. *Lab. Invest.* 79, 619-620 (1999).
19. Sawada, M., Hayes, P., & Matsuyama, S. Cytoprotective membrane-permeable peptides designed from the Bax-binding domain of Ku70. *Nat. Cell Biol.* 5, 352-357 (2003).
20. As yet unpublished reference expected to be published at the same time as a manuscript containing the above working example.
21. Gong, Y. H., Parsadanian, A. S., Andreeva, A., Snider, W. D., & Elliott, J. L. Restricted expression of G86R Cu/Zn superoxide dismutase in astrocytes results in astrocytosis but does not cause motoneuron degeneration. *J. Neurosci.* 20, 660-665 (2000).
22. Wang, J. et al. Coincident thresholds of mutant protein for paralytic disease and protein aggregation caused by restrictively expressed superoxide dismutase cDNA. *Neurobiol. Dis.* 20, 943-952 (2005).
23. Kuo, J. J., Siddique, T., Fu, R., & Heckman, C. J. Increased persistent Na(+) current and its effect on excitability in motoneurones cultured from mutant SOD1 mice. *J. Physiol* 563, 843-854 (2005).
24. Zona, C., Pieri, M., & Carunchio, I. Voltage-dependent sodium channels in spinal cord motor neurons display rapid recovery from fast inactivation in a mouse model of amyotrophic lateral sclerosis. *J. Neurophysiol.* 96, 3314-3322 (2006).
25. Ricart, K. et al. Interactions between beta-neuregulin and neurotrophins in motor neuron apoptosis. *J Neurochem* 97, 222-233 (2006).
26. Gould, T. W. et al. Complete dissociation of motor neuron death from motor dysfunction by Bax deletion in a mouse model of ALS. *J. Neurosci.* 26, 8774-8786 (2006).
27. Shin, J. Y. et al. Expression of mutant huntingtin in glial cells contributes to neuronal excitotoxicity. *J. Cell Biol.* 171, 1001-1012 (2005).
28. Howland, D. S. et al. Focal loss of the glutamate transporter EAAT2 in a transgenic rat model of SOD1 mutant-mediated amyotrophic lateral sclerosis (ALS). *Proc. Natl. Acad. Sci. USA* 99, 1604-1609 (2002).
29. Scheffler, B. et al. Functional network integration of embryonic stem cell-derived astrocytes in hippocampal slice cultures. *Development* 130, 5533-5541 (2003).

30. Lukas, T. J., Luo, W. W., Mao, H., Cole, N., & Siddique, T. Informatics-assisted protein profiling in a transgenic mouse model of amyotrophic lateral sclerosis. *Mol. Cell Proteomics.* 5, 1233-1244 (2006).
31. Silva, G. A., Feeney, C., Mills, L. R., & Theriault, E. A novel and rapid method for culturing pure rat spinal cord astrocytes on untreated glass. *J Neurosci Methods* 80, 75-79 (1998).
32. Chalazonitis, A., Kessler, J. A., Twardzik, D. R., & Morrison, R. S. Transforming growth factor alpha, but not epidermal growth factor, promotes the survival of sensory neurons in vitro. *J. Neurosci.* 12, 583-594 (1992).
33. Chalazonitis, A., Crain, S. M., & Kessler, J. A. Preferential cholinergic projections by embryonic spinal cord neurons within cocultured mouse superior cervical ganglia. *Brain Res.* 458, 231-248 (1988).
34. Rideout, H. J., Dietrich, P., Wang, Q., Dauer, W. T., & Stefanis, L. alpha-synuclein is required for the fibrillar nature of ubiquitinated inclusions induced by proteasomal inhibition in primary neurons. *J. Biol. Chem.* 279, 46915-46920 (2004).
35. Kaji, K. & Matsuo, M. Aging of chick embryo fibroblasts in vitro. III. Polyploid cell accumulation. *Exp. Cell Res.* 119, 231-236 (1979).
36. Przedborski, S. et al. Increased superoxide dismutase activity improves survival of cultured postnatal midbrain neurons. *J. Neurochem.* 67, 1383-1392 (1996).
37. Rowland L P. Hereditary and acquired motor neuron diseases. In: Merritt's textbook of neurology, edited by Rowland L P. Philadelphia: Williams & Wilkins, 1995, p. 742-749.
38. Mizutani T, Sakamaki S, Tsuchiya N, Kamei S, Kohzu H, Horiuchi R, Ida M, Shiozawa R and Takasu T. Amyotrophic lateral sclerosis with ophtalmoplegia and multisystem degeneration in patients on long-term use of respirators. Acta Neuropathol (Berl) 84: 372-377, 1992.
39. Hirano A. Neuropathology of ALS: an overview. Neurology 47: S63-S66, 1996.
40. Pasinelli P and Brown R H. Molecular biology of amyotrophic lateral sclerosis: insights from genetics. Nat Rev Neurosci 7: 710-723, 2006.
41. Hayward L J, Rodriguez J A, Kim J W, Tiwari A, Goto J J, Cabelli D E, Valentine J S and Brown R H, Jr. Decreased metallation and activity in subsets of mutant superoxide dismutases associated with familial amyotrophic lateral sclerosis. J Biol Chem 277: 15923-15931, 2002.
42. Halliwell B and Gutteridge J M. Free radicals in biology and medicine. Oxford: Clarendon Press, 1991.
43. Reaume A G, Elliott J L, Hoffman. E K, Kowall N W, Ferrante R J, Siwek D F, Wilcox H M, Flood D G, Beal M F, Brown R H, Jr., Scott R W and Snider W D. Motor neurons in Cu/Zn superoxide dismutase-deficient mice develop normally but exhibit enhanced cell death after axonal injury. Nat Genet 13: 43-47, 1996.
44. Wang J, Slunt H, Gonzales V, Fromholt D, Coonfield M, Copeland N G, Jenkins N A and Borchelt D R. Copper-binding-site-null SOD1 causes ALS in transgenic mice: aggregates of non-native SOD1 delineate a common feature. Hum Mol Genet 12: 2753-2764, 2003.
45. Wiedau-Pazos M, Goto J J, Rabizadeh S, Gralla E B, Roe J A, Lee M K, Valentine J S and Bredesen D E. Altered reactivity of superoxide dismutase in familial amyotrophic lateral sclerosis. Science 271: 515-518, 1996.
46. Yim M B, Kang J H, Yim H S, Kwak H S, Chock P B and Stadtman E R. A gain-of-function of an amyotrophic lateral sclerosis-associated Cu, Zn-superoxide dismutase mutant: An enhancement of free radical formation due to a decrease in Km for hydrogen peroxide. Proc Natl Acad Sci USA 93: 5709-5714, 1996.
47. Durham H D, Roy J, Dong L and Figlewicz D A. Aggregation of mutant Cu/Zn superoxide dismutase proteins in a culture model of ALS. J Neuropathol Exp Neurol 56: 523-530, 1997.
48. Kunst C B, Mezey E, Brownstein M J and Patterson D. Mutations in SOD1 associated with amyotrophic lateral sclerosis cause novel protein interactions. Nat Genet 15: 91-94, 1997.
49. Estevez A G, Crow J P, Sampson J B, Reiter C, Zhuang Y, Richardson G J, Tarpey M M, Barbeito L and Beckman J S. Induction of nitric oxide-dependent apoptosis in motor neurons by zinc-deficient superoxide dismutase. Science 286: 2498-2500, 1999.
50. Liu J, Lillo C, Jonsson P A, Vande Velde C, Ward C M, Miller T M, Subramaniam J R, Rothstein J D, Marklund S, Andersen P M, Brannstrom T, Gredal O, Wong P C, Williams D S and Cleveland D W. Toxicity of familial ALS-linked SOD1 mutants from selective recruitment to spinal mitochondria. Neuron 43: 5-17, 2004.
51. Li M, Ona V O, Guegan C, Chen M, Jackson-Lewis V, Andrews L J, Olszewski A J, Stieg P E, Lee J P, Przedborski S and Friedlander R M. Functional role of caspase-1 and caspase-3 in an ALS transgenic mouse model. Science 288: 335-339, 2000.
52. Clement A M, Nguyen M D, Roberts E A, Garcia M L, Boillee S, Rule M, McMahon A P, Doucette W, Siwek D, Ferrante R J, Brown R H, Jr., Julien J P, Goldstein L S B and Cleveland D W. Wild-Type Nonneuronal Cells Extend Survival of SOD1 Mutant Motor Neurons in ALS Mice. Science 302: 113-117, 2003.
53. Beers D R, Henkel J S, Xiao Q, Zhao W, Wang J, Yen A A, Siklos L, McKercher S R and Appel S H. Wild-type microglia extend survival in PU.1 knockout mice with familial amyotrophic lateral sclerosis. Proc Natl Acad Sci USA 103: 16021-16026, 2006.
54. Monani U R. Spinal muscular atrophy: a deficiency in a ubiquitous protein; a motor neuron-specific disease. Neuron 48: 885-896, 2005.
55. Lefebvre S, Burglen L, Reboullet S, Clermont O, Burlet P, Viollet L, Benichou B, Cruaud C, Millasseau P and Zeviani M. Identification and characterization of a spinal muscular atrophy-determining gene. Cell 80: 155-165, 1995.
56. Feldkotter M, Schwarzer V, Wirth R, Wienker T F and Wirth B. Quantitative analyses of SMN1 and SMN2 based on real-time lightCycler PCR: fast and highly reliable carrier testing and prediction of severity of spinal muscular atrophy. Am J Hum Genet 70: 358-368, 2002.
57. Monani U R, Sendtner M, Coovert D D, Parsons D W, Andreassi C, Le T T, Jablonka S, Schrank B, Rossol W, Prior T W, Morris G E and Burghes A H. The human centromeric survival motor neuron gene (SMN2) rescues embryonic lethality in Smn(−/−) mice and results in a mouse with spinal muscular atrophy. Hum Mol Genet 9: 333-339, 2000.
58. Vitte J M, Davoult B, Roblot N, Mayer M, Joshi V, Courageot S, Tronche F, Vadrot J, Moreau M H, Kemeny F and Melki J. Deletion of murine Smn exon 7 directed to liver leads to severe defect of liver development associated with iron overload. Am J Pathol 165: 1731-1741, 2004.
59. Meister G, Buhler D, Laggerbauer B, Zobawa M, Lottspeich F and Fischer U. Characterization of a nuclear 20S complex containing the survival of motor neurons (SMN) protein and a specific subset of spliceosomal Sm proteins. Hum Mol Genet 9: 1977-1986, 2000.
60. Pellizzoni L, Kataoka N, Charroux B and Dreyfuss G. A novel function for SMN, the spinal muscular atrophy disease gene product, in pre-mRNA splicing. Cell 95: 615-624, 1998.
61. Jones K W, Gorzynski K, Hales C M, Fischer U, Badbanchi F, Terns R M and Terns M P. Direct Interaction of the Spinal Muscular Atrophy Disease Protein SMN with the Small Nucleolar RNA-associated Protein Fibrillarin. J Biol Chem 276: 38645-38651, 2001.
62. Rossoll W, ning A K, Ohndorf U M, Steegborn C, Jablonka S and Sendtner M. Specific interaction of Smn, the spinal muscular atrophy determining gene product, with hnRNP-R and gry-rbp/hnRNP-Q: A role for Smn in RNA processing in motor axons? Hum Mol Genet 11: 93-105, 2002.
63. Gangwani L, Mikrut M, Theroux S, Sharma M and Davis R J. Spinal muscular atrophy disrupts the interaction of ZPR1 with the SMN protein. Nat Cell Biol 3: 376-383, 2001.
64. Williams B Y, Hamilton S L and Sarkar H K. The survival motor neuron protein interacts with the transactivator FUSE binding protein from human fetal brain. FEBS Lett 470: 207-210, 2000.
65. de Groot C J, Langeveld C H, Jongenelen C A, Montagne L, Van d, V and Dijkstra C D. Establishment of human adult astrocyte cultures derived from postmortem multiple sclerosis and control brain and spinal cord regions: immunophenotypical and functional characterization. *J Neurosci Res* 49: 342-354, 1997.
66. Fruger, T., et al., Nuclear targeting defect of SMN lacking the C-terminus in a mouse model of spinal muscular atrophy. Hm. Mol. Genet. 9:849-858 (2000).
67. Shin, S, et al., Stage dependent Olig2 expression in motor neurons and oligodendrocytes differentiated from embryonic stem cells. Stem Cells Dev. 16 (1): 131-41 (2007).
68. Shin, S., et al. Human Motomeural differentiation from human embryonic stem cells. Stem Cells Dev. 14:1-4 (2005).

Various references are cited herein, the contents of which are hereby incorporated by reference in their entireties.

What is claimed is:

1. A method for identifying an agent for treating a neurodegenerative condition associated with degeneration of motor neurons caused by soluble factors released by astrocytes carrying a SOD1 G93A mutation, comprising:
   i. subjecting embryonic stem cells to retinoic acid and sonic hedgehog agonist in vitro, for five days, to produce a-motor neuron cells;
   ii. plating the motor neuron cells in neurobasal medium containing 2% heat inactivated horse serum, B27 supplement, 0.5 mM glutamine, 25 μM 2-mercaptoethanol, and penicillin/streptomycin and adding a degeneration-promoting astrocyte carrying a SOD1 G93A mutation or a conditioned medium produced by a culture of degeneration-promoting astrocytes carrying a SOD1 G93A mutation, so as to establish a culture system comprising the motor neuron and a degeneration-promoting astrocyte carrying a SOD1 G93A mutation or a conditioned medium produced by a culture of degeneration-promoting astrocytes carrying a SOD1 G93A mutation;
   iii. adding the agent to the culture system;
   iv. subjecting the culture system to a time period of culturing of at least 2 days;
   v. evaluating whether the motor neuron in the culture system degenerates in the presence of the agent, wherein the evaluation of degeneration is relative to a control culture system comprising identically produced motor neurons subjected to the same time period of culturing in the absence of the agent; and
   vi. determining if the agent reduces degeneration of the motor neurons by comparing the number of dead neurons present in the culture system containing the agent to the number of dead neurons in the control culture system.

2. The method of claim 1, wherein the embryonic stem cell and degeneration-promoting astrocyte are from a mouse.

3. A method for identifying an agent for treating amyotrophic lateral sclerosis caused by soluble factors released by astrocytes carrying a SOD1 G93A mutation, comprising:
   i. subjecting embryonic stem cells to retinoic acid and sonic hedgehog agonist in vitro, for five days, to produce a-motor neuron cells;
   ii. plating the motor neuron cells in neurobasal medium containing 2% heat inactivated horse serum, B27 supplement, 0.5 mM glutamine, 25 μM 2-mercaptoethanol, and penicillin/streptomycin and adding a degeneration-promoting astrocyte carrying a SOD1 G93A mutation or a conditioned medium produced by a culture of degeneration-promoting astrocytes carrying a SOD1 G93A mutation, so as to establish a culture system comprising the motor neuron and a degeneration-promoting astrocyte carrying a SOD1 G93A mutation or a conditioned medium produced by a culture of degeneration-promoting astrocytes carrying a SOD1 G93A mutation;
   iii. adding the agent to the culture system;
   iv. subjecting the culture system to a time period of culturing of at least 2 days;
   v. evaluating whether the motor neuron in the culture system degenerates in the presence of the agent, wherein the evaluation of degeneration is relative to a control culture system comprising identically produced motor neurons subjected to the same time period of culturing in the absence of the agent; and
   vi. determining if the agent reduces degeneration of the motor neurons by comparing the number of dead neurons present in the culture system containing the agent to the number of dead neurons in the control culture system.

4. The method of claim 3, wherein the degeneration-promoting astrocyte was obtained from an individual suffering from amyotrophic lateral sclerosis.

* * * * *